(12) United States Patent
Lebel et al.

(10) Patent No.: US 7,024,245 B2
(45) Date of Patent: Apr. 4, 2006

(54) AMBULATORY MEDICAL APPARATUS AND METHOD USING A ROBUST COMMUNICATION PROTOCOL

(75) Inventors: Ronald J. Lebel, Sherman Oaks, CA (US); Varaz Shahmirian, Northridge, CA (US); Sam W. Bowman, IV, Valencia, CA (US); Robert C. Dennard, Lancaster, CA (US); John T. Armstrong, Pasadena, CA (US); John D. Richert, La Habra Heights, CA (US)

(73) Assignee: Medtronic Minimed, Inc., Northridge, CA (US)

( * ) Notice: Subject to any disclaimer, the term of this patent is extended or adjusted under 35 U.S.C. 154(b) by 154 days.

(21) Appl. No.: 10/843,196

(22) Filed: May 11, 2004

(65) Prior Publication Data

US 2004/0210267 A1 Oct. 21, 2004

Related U.S. Application Data

(62) Division of application No. 09/768,043, filed on Jan. 22, 2001, now Pat. No. 6,813,519.
(60) Provisional application No. 60/177,414, filed on Jan. 21, 2000.

(51) Int. Cl.
*A61N 1/18* (2006.01)
*A61N 1/20* (2006.01)

(52) U.S. Cl. ............................................. 607/32; 607/9

(58) Field of Classification Search ................... 607/32, 607/9, 2, 17, 18, 19, 25, 27, 28, 29, 30, 31; 600/300; 340/573.1–573.4; 434/258; 604/131, 604/132; 128/903, 904
See application file for complete search history.

(56) References Cited

U.S. PATENT DOCUMENTS

| 3,910,257 A | * | 10/1975 | Fletcher ....................... 600/483 |
| 4,854,328 A | * | 8/1989 | Pollack ....................... 600/549 |
| 5,127,404 A | | 7/1992 | Wyborny et al. |

(Continued)

FOREIGN PATENT DOCUMENTS

| EP | 0 346 783 | 6/1989 |
| EP | 0 832 600 A1 | 4/1998 |
| EP | 0 920 885 A1 | 6/1999 |
| WO | 97/18639 | 5/1997 |

OTHER PUBLICATIONS

PCT International Search Report as issued in International Application No. PCT/US01/23003, Mailing Date Jul. 3, 2002.
PCT International Search Report as issued in International Application No. PCT/US01/22926, Mailing Date Jul. 8, 2002.

*Primary Examiner*—Daniel Robinson
(74) *Attorney, Agent, or Firm*—Foley & Lardner LLP

(57) ABSTRACT

An implanted medical device (e.g. infusion pump) and external device communicate with one another via telemetry wherein messages are transmitted under a robust communication protocol. The communication protocol gives enhanced assurance concerning the integrity of messages that impact medical operations of the implantable device. Messages are transmitted using a multipart format that includes a preamble, a frame sync, a telemetry ID, data, and a validation code. The data portion of the message includes an op-code that dictates various other elements that form part of the message. The data portion may also include additional elements such as sequence numbers, bolus numbers, and duplicate data elements. A telemetry ID for the transmitting device may be implicitly embedded in the message as part of the validation code that is sent with the message and that must be pre-known by the receiver to confirm the integrity of the received message.

42 Claims, 3 Drawing Sheets

U.S. PATENT DOCUMENTS

| | | |
|---|---|---|
| 5,191,326 A | 3/1993 | Montgomery |
| 5,231,988 A * | 8/1993 | Wernicke et al. ........... 607/118 |
| 5,416,695 A | 5/1995 | Stutman et al. |
| 5,438,621 A | 8/1995 | Hornak et al. |
| 5,659,299 A | 8/1997 | Williamson et al. |
| 5,718,234 A | 2/1998 | Warden et al. |
| 5,730,125 A | 3/1998 | Prutchi et al. |
| 5,752,976 A * | 5/1998 | Duffin et al. .................. 607/32 |
| 5,791,344 A * | 8/1998 | Schulman et al. .......... 600/347 |
| 5,974,341 A | 10/1999 | Er et al. |
| 6,026,124 A | 2/2000 | Lee et al. |
| 6,208,894 B1 * | 3/2001 | Schulman et al. ............. 607/2 |
| 6,353,406 B1 * | 3/2002 | Lanzl et al. ................. 342/118 |
| 6,554,798 B1 * | 4/2003 | Mann et al. ................ 604/131 |

\* cited by examiner

AMBULATORY MEDICAL APPARATUS AND METHOD USING A ROBUST COMMUNICATION PROTOCOL

RELATED APPLICATIONS

This application is a divisional of application Ser. No. 09/768,043 filed Jan. 22, 2001, now U.S. Pat. No. 6,813,519 which is in turn claims the benefit of prior filed U.S. Provisional Patent Application No. 60/177,414; filed Jan. 21, 2000. The entirety of each which are incorporated herein by reference.

FIELD OF THE DISCLOSURE

This invention relates generally to ambulatory medical systems that include a medical device and a control device that communicate via telemetry and more particularly to devices that exchange messages using a robust telemetry protocol. Preferred embodiments relate to implantable infusion pumps and external devices for communicating therewith.

BACKGROUND

Various ambulatory medical devices have been proposed and a number of such devices are commercially available. These devices include, for example, implantable infusion pumps, externally carried infusion pumps, implantable pacemakers, implantable defibrillators, implantable neural stimulators, implantable physiological sensors, externally carried physiologic sensors, and the like.

Numerous electronic devices exist that communicate with one another using electromagnetic radiation of various wavelengths and of various formats. These electronic devices can act as sources of interference that can negatively impact other devices that also need to communicate via telemetry. This is particularly true when other devices attempt to communicate using small signal strengths that are typically associated with the limited power that is available to ambulatory medical devices and most particular to ambulatory devices that are implanted within the body of a patient.

As appropriate operation of medical devices may be critical to those patients being treated using those devices, and as telemetry communications between medical devices and external controllers can greatly enhance the convenience of using such devices, or even be an enabling necessity to the use of such devices (e.g. implantable devices with sophisticated functionality), the operation of such medical devices can benefit significantly by use of telemetry systems and protocols that have features/elements that lead to optimization of various attributes. Attributes of interest may vary with circumstance but some attributes of general interest include (1) flexibility in communicating the wide variety signals that may be useful to controlling and retrieving information from a sophisticated medical device, (2) robustness in distinguishing actual signals from noise, (3) robustness in distinguishing valid signals from corrupt signals, (4) robustness in ascertaining when appropriate communication has occurred and when additional communication must be attempted, (5) a reasonable efficiency in communication time, and/or (6) a reasonable efficiency in electrical power consumption associated with conveying information over the telemetry system.

For example, implantable infusion pumps are generally configured to accept infusion commands from an external communication device via an RF telemetry system, or the like. These commands may be used, inter alia, to set program variables that are in turn used in defining the quantity and/or timing that is used in supplying a drug to the patient. As the dispensing of appropriate amounts of the drug may be critical to the patient's well being, it is desirable that a reliable and trustworthy communication channel exist between the external communication device and the implantable device so that messages from the external communication device requesting drug delivery are received with integrity, confirmation of accurate reception acknowledged in a rapid manner, and minimal electric power consumption occurring in the entire process of listening for a message, receiving the message, and transmitting a response to the message that is appropriately received by the external communication device.

Implantable medical devices typically operate by battery power. The batteries may or may not be rechargeable. Higher consumption of power from an implantable medical device containing non-rechargeable batteries leads to a shortening of the usable life of the device and an associated increased frequency of surgery, potential pain, recovery, and inconvenience. Higher consumption of power from an implantable medical device containing rechargeable batteries leads to more frequent charging periods for the batteries and associated inconvenience and may lead to an overall shortening of the usable life of the device. As such, whether or not an implantable medical device contains rechargeable batteries or non-rechargeable batteries, it is desirable to lower the power consumption of the device. As telemetry reception and transmission are highly energy consumptive, it is desirable to minimize the operation time of telemetry reception and transmission modules. As such it is desirable to ensure that message length is kept to a minimum and that repeated transmissions and attempted receptions of previously sent but unsuccessfully received messages be kept to a minimum.

A need exists in the field for improved telemetry features/elements that tend to optimize each of the above noted attributes individually, with out consideration of the impact on other attributes, or tend to simultaneously optimize groups of selected attributes, or tend to provide a balance between various ones of the attributes.

SUMMARY OF THE INVENTION

It is a first object of certain aspects of the invention to enhance the ability to communicate a wide variety signals that are useful in controlling and retrieving information from an ambulatory medical device.

It is a second object of certain aspects of the invention to enhance the robustness of distinguishing actual signals from when receiving telemetry communications in an ambulatory medical system.

It is a third object of certain aspects of the invention to enhance the robustness of distinguishing valid signals corrupt signals when receiving telemetry communications in an ambulatory medical system.

It is a fourth object of certain aspects of the invention to enhance the robustness of ascertaining when appropriate communication has occurred and when additional communication must be attempted in an ambulatory medical system.

It is a fifth object of certain aspects of the invention to decrease the time that is spent in transmitting and receiving messages using a telemetry system in an ambulatory medical system.

It is a sixth object of certain aspects of the invention to decrease the electrical power consumption associated with conveying a given amount of information via telemetry in an ambulatory medical system.

Other objects and advantages of various aspects of the invention will be apparent to those of skill in the art upon review of the teachings herein. The various aspects of the invention set forth below as well as other aspects of the invention not specifically set forth below but ascertained from the teachings found herein, may address the above noted objects or other objects ascertained from the teachings herein individually or in various combinations. As such, it is intended that each aspect of the invention address at least one of the above noted objects or address some other object that will be apparent to one of skill in the art from a review of the teachings herein. It is not intended that all, or even a portion of these objects, necessarily be addressed by any single aspect of the invention even though that may be the case with regard to some aspects.

A first aspect of the invention provides a medical system that includes (a) an ambulatory medical device (MD) that includes MD electronic control circuitry that further includes at least one MD telemetry system and at least one MD processor that controls, at least in part, operation of the MD telemetry system and operation of the medical device, wherein the medical device is configured to provide a treatment to a body of a patient or to monitor a selected state of the body; and (b) a communication device (CD) that includes CD electronic control circuitry that further includes at least one CD telemetry system and at least one CD processor that controls, at least in part, operation of the CD telemetry system and operation of the communication device, wherein the CD telemetry system sends messages to or receives messages from the MD telemetry system, wherein at least a portion of the messages transmitted between the communication device and the medical device are transmitted using a message structure that includes a preamble, a telemetry identifier, and data.

In a specific variation of the first aspect of the invention, the CD telemetry system sends messages to the MD telemetry system using a message structure that comprises: (1) an MD preamble, (2) an MD telemetry identifier, (3) MD data including an op-code, and (4) an MD validation code.

In another specific variation of the first aspect of the invention, the MD telemetry system sends messages to the CD telemetry system using a message structure that comprises: (1) a CD preamble, (2) a CD telemetry identifier, (3) CD data including a CD op-code, and (4) a CD validation code.

A second aspect of the invention provides a medical system that includes (a) an ambulatory medical device (MD) that includes MD electronic control circuitry that further includes at least one MD telemetry system and at least one MD processor that controls, at least in part, operation of the MD telemetry system and operation of the medical device, wherein the medical device is configured to provide a treatment to a body of a patient or to monitor a selected state of the body; and (b) a communication device (CD) that includes CD electronic control circuitry that further includes at least one CD telemetry system and at least one CD processor that controls, at least in part, operation of the CD telemetry system and operation of the communication device, wherein the CD telemetry system sends messages to or receives messages from the MD telemetry system, wherein at least a portion of the messages sent between the communication device and the medical device are directed to specific medical device, or a specific communication device, by inclusion of an MD identifier that identifies the medical device or a CD identifier that identifies the communication device.

A third aspect of the invention provides a medical system that includes (a) an ambulatory medical device (MD) that includes MD electronic control circuitry that further includes at least one MD telemetry system and at least one MD processor that controls, at least in part, operation of the MD telemetry system and operation of the medical device, wherein the medical device is configured to provide a treatment to a body of a patient or to monitor a selected state of the body; and (b) a communication device (CD) that includes CD electronic control circuitry that further includes at least one CD telemetry system and at least one CD processor that controls, at least in part, operation of the CD telemetry system and operation of the communication device, wherein the CD telemetry system sends messages to or receives messages from the MD telemetry system, wherein the integrity of at least a portion of a message passed between the communication device and medical device is confirmed by analysis of a predefined interrelation between at least two portions of the message.

A fourth aspect of the invention provides a medical system that includes (a) an ambulatory medical device (MD) that includes MD electronic control circuitry that further includes at least one MD telemetry system and at least one MD processor that controls, at least in part, operation of the MD telemetry system and operation of the medical device, wherein the medical device is configured to provide a treatment to a body of a patient or to monitor a selected state of the body; and (b) a communication device (CD) that includes CD electronic control circuitry that further includes at least one CD telemetry system and at least one CD processor that controls, at least in part, operation of the CD telemetry system and operation of the communication device, wherein the CD telemetry system sends messages to or receives messages from the MD telemetry system, wherein at least one of the medical device or the communication device acts as a sender to transmit a message to the other of the communication device or the medical device, which is the intended receiver of the message, wherein the message is sent with a validation code that is derived in part from the content of the message and in part from other information not explicitly transmitted in the message, and wherein the other information is known in advance by the receiver and is used by the receiver in determining that the message was received without error.

A fifth aspect of the invention provides a medical system that includes (a) an ambulatory medical device (MD) that includes MD electronic control circuitry that further includes at least one MD telemetry system and at least one MD processor that controls, at least in part, operation of the MD telemetry system and operation of the medical device, wherein the medical device is configured to provide a treatment to a body of a patient or to monitor a selected state of the body; and (b) a communication device (CD) that includes CD electronic control circuitry that further includes at least one CD telemetry system and at least one CD processor that controls, at least in part, operation of the CD telemetry system and operation of the communication device, wherein the CD telemetry system sends messages to or receives messages from the MD telemetry system, wherein a message is sent using one of a predefined plurality of preambles.

A sixth aspect of the invention provides a medical system that includes (a) an ambulatory medical device (MD) that includes MD electronic control circuitry that further includes at least one MD telemetry system and at least one MD processor that controls, at least in part, operation of the MD telemetry system and operation of the medical device, wherein the medical device is configured to provide a treatment to a body of a patient or to monitor a selected state of the body; and (b) a communication device (CD) that includes CD electronic control circuitry that further includes at least one CD telemetry system and at least one CD processor that controls, at least in part, operation of the CD telemetry system and operation of the communication device, wherein the CD telemetry system sends messages to or receives messages from the MD telemetry system, wherein the communication device has a CD telemetry identifier and the medical device has a MD telemetry identifier wherein the length of the CD telemetry and MD telemetry identifiers are different.

A seventh aspect of the invention provides a medical system that includes (a) an ambulatory medical device (MD) that includes MD electronic control circuitry that further includes at least one MD telemetry system and at least one MD processor that controls, at least in part, operation of the MD telemetry system and operation of the medical device, wherein the medical device is configured to provide a treatment to a body of a patient or to monitor a selected state of the body; and (b) a communication device (CD) that includes CD electronic control circuitry that further includes at least one CD telemetry system and at least one CD processor that controls, at least in part, operation of the CD telemetry system and operation of the communication device, wherein the CD telemetry system sends messages to or receives messages from the MD telemetry system, wherein the MD telemetry system is configured to perform a bit pattern recognition that allows a selected level of fault tolerance in concluding that a selected portion of a message matches an expected pattern to be received.

A eighth aspect of the invention provides a medical system that includes (a) an ambulatory medical device (MD) that includes MD electronic control circuitry that further includes at least one MD telemetry system and at least one MD processor that controls, at least in part, operation of the MD telemetry system and operation of the medical device, wherein the medical device is configured to provide a treatment to a body of a patient or to monitor a selected state of the body; and (b) a communication device (CD) that includes CD electronic control circuitry that further includes at least one CD telemetry system and at least one CD processor that controls, at least in part, operation of the CD telemetry system and operation of the communication device, wherein the CD telemetry system sends messages to or receives messages from the MD telemetry system, wherein at least one of the MD telemetry system or the CD telemetry system is configured to establish bit synchronization using bit information transmitted in a preamble portion of a message and uses a different pattern to establish synchronization for groups of bits.

An ninth aspect of the invention provides a medical system that includes (a) an ambulatory medical device (MD) that includes MD electronic control circuitry that further includes at least one MD telemetry system and at least one MD processor that controls, at least in part, operation of the MD telemetry system and operation of the medical device, wherein the medical device is configured to provide a treatment to a body of a patient or to monitor a selected state of the body; and (b) a communication device (CD) that includes CD electronic control circuitry that further includes at least one CD telemetry system and at least one CD processor that controls, at least in part, operation of the CD telemetry system and operation of the communication device, wherein the CD telemetry system sends messages to or receives messages from the MD telemetry system, wherein at least one of the MD telemetry system or the CD telemetry system is configured to establish frame synchronization and to confirm that a message is intended specifically for the medical device or the communication device, respectively, by confirming receipt of a predefined identifier.

An tenth aspect of the invention provides a medical system that includes (a) an ambulatory medical device (MD) that includes MD electronic control circuitry that further includes at least one MD telemetry system and at least one MD processor that controls, at least in part, operation of the MD telemetry system and operation of the medical device, wherein the medical device is configured to provide a treatment to a body of a patient or to monitor a selected state of the body; and (b) a communication device (CD) that includes CD electronic control circuitry that further includes at least one CD telemetry system and at least one CD processor that controls, at least in part, operation of the CD telemetry system and operation of the communication device, wherein the CD telemetry system sends messages to or receives messages from the MD telemetry system, wherein selected messages sent between the MD telemetry system and the CD telemetry system comprise character patterns that are incremented in relationship to corresponding character patterns included in one or more previous messages.

In a specific variation of the tenth aspect of the invention, the character patterns are sequence numbers that are varied between first and second messages that are varied within a receiver when they are successfully received and varied within a transmitter when the transmitter receives confirmation that the message was successfully received.

A eleventh aspect of the invention provides a medical system that includes (a) an ambulatory medical device (MD) that includes MD electronic control circuitry that further includes at least one MD telemetry system and at least one MD processor that controls, at least in part, operation of the MD telemetry system and operation of the medical device, wherein the medical device is configured to provide a treatment to a body of a patient or to monitor a selected state of the body; and (b) a communication device (CD) that includes CD electronic control circuitry that further includes at least one CD telemetry system and at least one CD processor that controls, at least in part, operation of the CD telemetry system and operation of the communication device, wherein the CD telemetry system sends messages to or receives messages from the MD telemetry system, wherein the communication device requires pre-knowledge of a telemetry identifier for the medical device prior to sending any messages to the medical device that can be used by the medical device to significantly modify the medical functioning of the medical device, or wherein the medical device requires pre-knowledge of a telemetry identifier for the communication device prior to the medical device accepting any messages from the communication device that can be used by the medical device to significantly modify the medical functioning of the medical device.

A twelfth aspect of the invention provides a medical system that includes (a) an ambulatory medical device (MD) that includes MD electronic control circuitry that further includes at least one MD telemetry system and at least one MD processor that controls, at least in part, operation of the MD telemetry system and operation of the medical device, wherein the medical device is configured to provide a treatment to a body of a patient or to monitor a selected state of the body; (b) a communication device (CD) that includes CD electronic control circuitry that further includes at least one CD telemetry system and at least one CD processor that controls, at least in part, operation of the CD telemetry system and operation of the communication device, wherein the CD telemetry system sends messages to or receives messages from the MD telemetry system; and (c) a second device (SD) including at least one infrared SD communication system, wherein the and CD telemetry system and the MD telemetry system are RF telemetry systems, and wherein the communication device further comprises an infrared CD communication system for sending messages to or receiving messages from the SD communication system.

A thirteenth aspect of the invention provides a medical system that includes (a) an ambulatory medical device (MD) that includes MD electronic control circuitry that further includes at least one MD telemetry system and at least one MD processor that controls, at least in part, operation of the MD telemetry system and operation of the medical device, wherein the medical device is configured to provide a treatment to a body of a patient or to monitor a selected state of the body; (b) a communication device (CD) that includes CD electronic control circuitry that further includes at least one CD telemetry system and at least one CD processor that controls, at least in part, operation of the CD telemetry system and operation of the communication device, wherein the CD telemetry system sends messages to or receives messages from the MD telemetry system, wherein a message is sent by the communication device to the medical device using a first frame synchronization pattern and wherein a message sent by the medical device to the communication device is sent with a second frame synchronization pattern which is different from the first pattern.

Additional specific variations, provide the medical devices of each of the above aspects and above noted variations as implantable devices such as implantable infusion pumps, implantable physiological sensors, implantable stimulators, and the like, or external devices such as subcutaneous delivery infusion pumps or sensors that ascertain a physiological parameter or parameters from subcutaneous tissue or from the skin of the patient. Such infusion pumps may dispense insulin, analgesics, neurological drugs, drugs for treating AIDS, drugs for treating chronic ailments or acute ailments. Sensors may be used to detect various physiological parameters such as hormone levels, insulin, pH, oxygen, other blood chemical constituent levels, and the like. The sensor may be of the electrochemical type, optical type, and may or may not be enzymatic in operation.

In even further variations of the above noted aspects, and above noted variations, one or more of the following is provided: (1) a first portion of the MD telemetry system is incorporated into the MD processor and a second portion of the MD telemetry system is external to the MD processor, (2) a first portion of the CD telemetry system is incorporated into the CD processor and a second portion of the CD telemetry system is external to the CD processor, (3) the MD processor includes an MD central processing unit and at least one other MD functional module, (4) the CD processor includes a CD central processing unit and at least one other CD functional module, (5) the MD electronic control circuitry includes at least one external MD functional module, other than a portion of the MD telemetry system, that is external to the MD processor, or (6) the CD electronic control circuitry includes at least one external CD functional module, other than a portion of the CD telemetry system, that is external to the CD processor.

Still additional aspects of the invention set forth method counterparts to the above system aspects as well as to other functional associations and relationships, and processes that have not been specifically set forth above but will be understood by those of skill in the art from a review of the teachings provided herein.

Further aspects of the invention will be understood by those of skill in the art upon reviewing the teachings herein. These other aspects of the invention may provide various combinations of the aspects presented above as well as provide other configurations, structures, functional relationships, and processes that have not been specifically set forth above.

BRIEF DESCRIPTION OF THE DRAWINGS

The above referred to objects and aspects of the present invention will be further understood from a review of the description to follow, the accompanying drawings, and the claims set forth hereafter, wherein:

DETAILED DESCRIPTION OF PREFERRED EMBODIMENTS

Figure 1A:
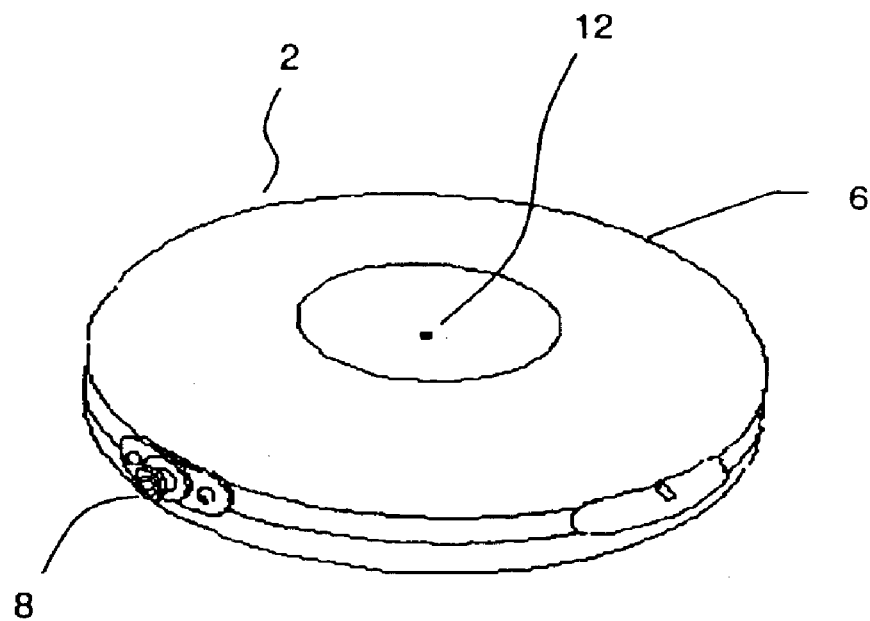
FIG. 1a depicts a perspective view of the main body of the implantable device of the first preferred embodiment.

Various details about the structural and functional configuration and operation of preferred ambulatory medical devices and preferred communication devices are found in several U.S. patent applications filed concurrently herewith and incorporated herein by reference in their entireties: (1) Ser. No. 09/768,045, (2) Ser. No. 09/768,206, (3) Ser. No. 09/768,198, (4) Ser. No. 09/768,207, and (5) Ser. No. 09/768,221.

U.S. patent application Ser. No. 09/768,045 filed on Jan. 22, 2001 (concurrently herewith), by Starkweather, et al., entitled "*Ambulatory Medical Apparatus and Method Having Telemetry Modifiable Control Software*", corresponding to *Medtronic MiniMed, Inc.,* is hereby incorporated herein by this reference as if set forth in full herein. This application provides teachings concerning an implantable medical device (e.g. infusion pump) and handheld communication device wherein the implantable device is capable of operating under control of different software programs, wherein a first program operates after resetting the implantable device and is not capable of allowing significant medical functionality but is capable of selected telemetry operations including telemetry operations that allow replacement software to be downloaded, and wherein a second program may be caused to take control of the device and enables medical functionality and selected telemetry operations but is incapable of receiving replacement software. It is also taught that a software image may be received in multiple messages where each message is provided with its own validation code and wherein a validation code for the whole image is provided and wherein each provided validation code must compared to a derived validation code prior to accepting the validity of the replacement software.

U.S. patent application Ser. No. 09/768,206, filed on Jan. 22, 2001 (concurrently herewith), by Bowman, et al., entitled "*Ambulatory Medical Apparatus and Method using* a Telemetry System with Predefined Reception Listening Periods", corresponding to Medtronic MiniMed, Inc., is hereby incorporated herein by the reference as if set forth in full herein. This application provides teachings concerning an implantable medical device (e.g. infusion pump) and an external device that communicate with one another via telemetry messages that are receivable only during listening windows. Each listening window is open for a prescribed listening period and is spaced from other listening windows by an interval. The listening period is typically kept small to minimize power consumption. To increase likelihood of successful communication, the window may be forced to an open state, by use of an attention signal, in anticipation of an incoming message. To further minimize power consumption, it is desirable to minimize use of extended attention signals, and this is accomplished by the transmitter maintaining an estimate of prescribed listening start times and attempting to send messages only during listening periods. In the communication device, the estimate is updated as a result of information obtained with the reception of each message from the medical device.

U.S. patent application Ser. No. 09/768,198, filed on Jan. 22, 2001 (concurrently herewith), by Lebel, et al., entitled "Ambulatory Medical Apparatus with Hand Held Communication Device", corresponding to Medtronic MiniMed, Inc. is hereby incorporated herein by this reference as if set forth in full herein. This application provides teachings concerning an implantable medical device (e.g. infusion pump) and handheld communication device (CD) that exchange messages via telemetry such that commands are supplied to the implantable device and operational information is obtained therefrom. The CD is controlled, at least in part, by a processor IC according to a software program operating therein and provides feedback to a user via a visual display, an audio alarm, and a vibrational alarm, and allows input from the user via a touch sensitive keypad. Certain input functions are restricted by password. The visual display includes an icon and fixed element display region and a bitmap display region. The fixed element display region includes time and date displays, battery and drug level displays that decrement, and a moving delivery state display. Various screens allow operational or log information to be displayed and/or user entry of commands. Program features when disable are removed from a series of screen options that can be scrolled through.

U.S. patent application Ser. No. 09/768,207, filed on Jan. 22, 2001 (concurrently herewith), by Starkweather, et al., entitled "Method and Apparatus for Communicating Between an Ambulatory Medical Device and Control Device Via Telemetry Using Randomized Data", corresponding to Medtronic MiniMed, Inc., is hereby incorporated herein by this reference as if set forth in full herein. This application provides teachings concerning an implantable medical device (e.g. infusion pump) and handheld communication device that communicate with one another via telemetry wherein transmitted messages have enhanced numbers of and/or regularity of bit transitions to minimize the risk of synchronization loss between transmitted bits of data and received bits of data. It is taught that bit transitions for portions of messages may be enhanced by applying a pseudo-randomization scheme to those portions of messages that are transmitted in a way that allows the receiver to extract the original data from the received randomized data. Preferred randomization techniques modify (i.e. randomize) the data using a CRC value that is being accumulated while simultaneously causing the modified data to modify subsequent accumulation of the CRC itself. Upon reception, the reversal of data randomization is then made to occur so that the intended message is appropriately received.

U.S. patent application Ser. No. 09/768,221, filed on Jan. 22, 2001 (concurrently herewith), by Lebel, et al., entitled "Microprocessor Controlled Ambulatory Medical Apparatus with Hand Held Communication Device", corresponding to Medtromc MiniMed, Inc., is hereby incorporated herein by this reference as if set forth in full herein. This application provides teachings concerning an implantable medical device (e.g. infusion pump) and handheld communication device, wherein an implantable infusion pump possesses operational functionality that is, at least in part, controlled by software operating in two processor ICs which are configured to perform some different and some duplicate functions. The pump exchanges messages with the external communication device via telemetry. Each processor controls a different part of the drug infusion mechanism such that both processors must agree on the appropriateness of drug delivery for infusion to occur. Delivery accumulators are incremented and decremented with delivery requests and with deliveries made. When accumulated amounts reach or exceed, quantized deliverable amounts, infusion is made to occur. The accumulators are capable of being incremented by two or more independent types of delivery requests. Operational modes of the infusion device are changed automatically in view of various system errors that are trapped, various system alarm conditions that are detected, and when excess periods of time lapse between pump and external device interactions.

The first embodiment of the present invention provides a long term implantable medical delivery system that controllably supplies insulin to the body of a patient afflicted with diabetes mellitus. This embodiment includes an implantable medical device and an external communication device. In the most preferred embodiments, the communication device is a hand held device that is used directly by the patient to interact with the medical device as opposed to being limited to use by a physician, nurse, or technician. It is preferred that the communication device provide (1) the ability to send commands to the medical device, (2) receive information from the medical device, and (3) be able to present to the patient at least a portion of the information it receives from the medical device. In preferred embodiments, the patient interacts with the medical device via the communication device at least once per week, on average, more preferably at least once every other day, on average, and most preferably at least once per day, on average.

The implantable medical device (MD) includes a biocompatible housing; a reservoir within the housing for holding a quantity of insulin; a side port that attaches to the side of the housing, a catheter, that connects to the side port; a pumping mechanism, within the housing for moving the insulin from the reservoir through the sideport and through the catheter to the body of the patient; and control, monitoring, and communication electronics located within the housing. In alternative embodiments various portions of implantable medical device hardware may be located outside the housing. For example, the pumping mechanism or a telemetry antenna may be located within the sideport or other side mounted housing; or a telemetry antenna may mounted on the outside surface of the housing, or extend along the catheter The external communication device (CD) communicates commands to the medical device, receives information from the medical device, and communicates system status and system history to the patient. The external communication device includes a housing; a keypad mounted on the housing; a display forming part of the housing; and control, monitoring, and communication electronics located within the housing. In alternative embodiments, the keypad may be replaced in whole or in part by a touch sensitive display or a voice recognition system. In addition, or alternatively, the display may be replaced in whole or in part by a speech generation system or other audio communication system.

Figure 1B:
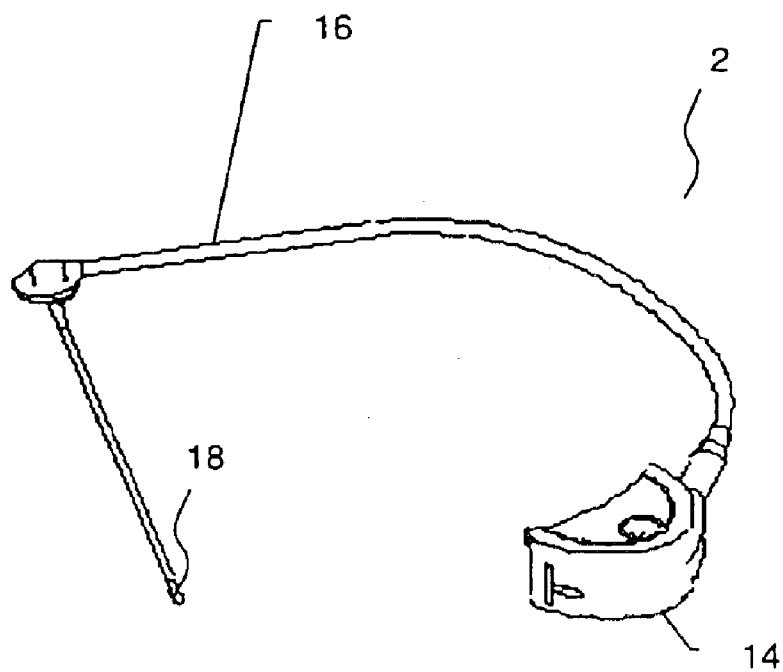
FIG. 1b depicts a perspective view of the support and catheter assembly that attaches to the main body of the implantable device of the first preferred embodiment.

The outer appearance of the implantable device 2 is depicted in two pieces in FIGS. 1*a* and 1*b* and includes housing 6 having a drug outlet port 8, and a refill port 12, a removable sideport 14 that mounts against the side of the housing 6 over outlet port 8, and a catheter 16 having a distal end 18 and a proximal end that attaches to sideport 14. In alternative embodiments, the implantable device may take on a different shape and/or the sideport may be removed in favor of a permanently mounted catheter assembly.

Figure 2:
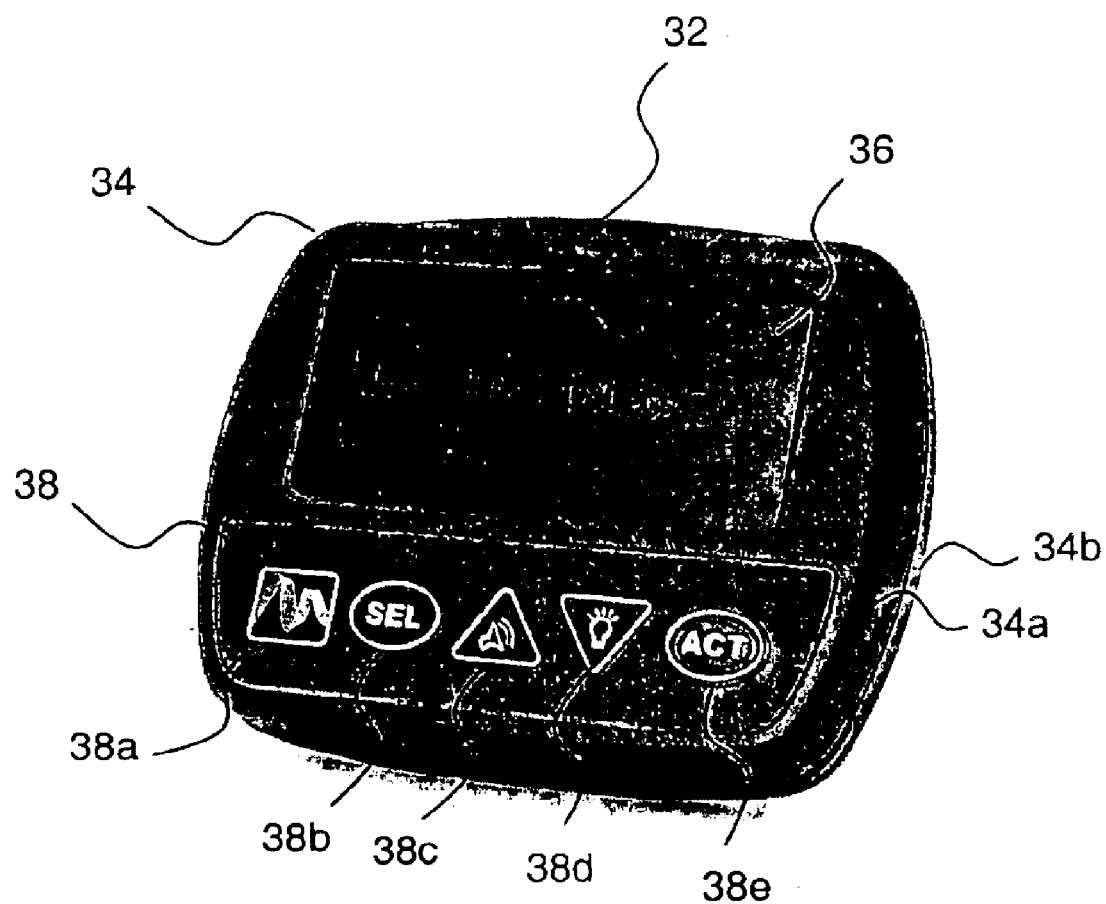
FIG. 2 depicts a perspective view of the external communication device of the first preferred embodiment.

The outer appearance of the external communication device 32 is depicted in FIG. 2. The various components of the external communication device are fitted in or on housing 34. Housing 34 is divided into a front portion 34*a* and a back portion 34*b*. The front portion 34*a* is provided with an opening in which an LCD panel 36 is positioned. The panel 36 has a lower portion that is a bit map display and an upper portion that provides icons and fixed element displays. The front portion 34*a* of the external communication device is also provided with a five-element keypad 38. A first key 38*a* is not located under a raised pad and does not provide tactile feedback when it is touched and may be used for special functions. The remaining four keys 38*b*, 38*c*, 38*d*, and 38*e* have raised pads that provide tactile feedback when they are depressed. These remaining keys may be used in normal device operation and are known as the select key, the up arrow key, down arrow key, and the activate key, respectively. The back portion 34*b* of the housing is fitted with a door under which a compartment is located for holding a replaceable battery.

Figure 3:
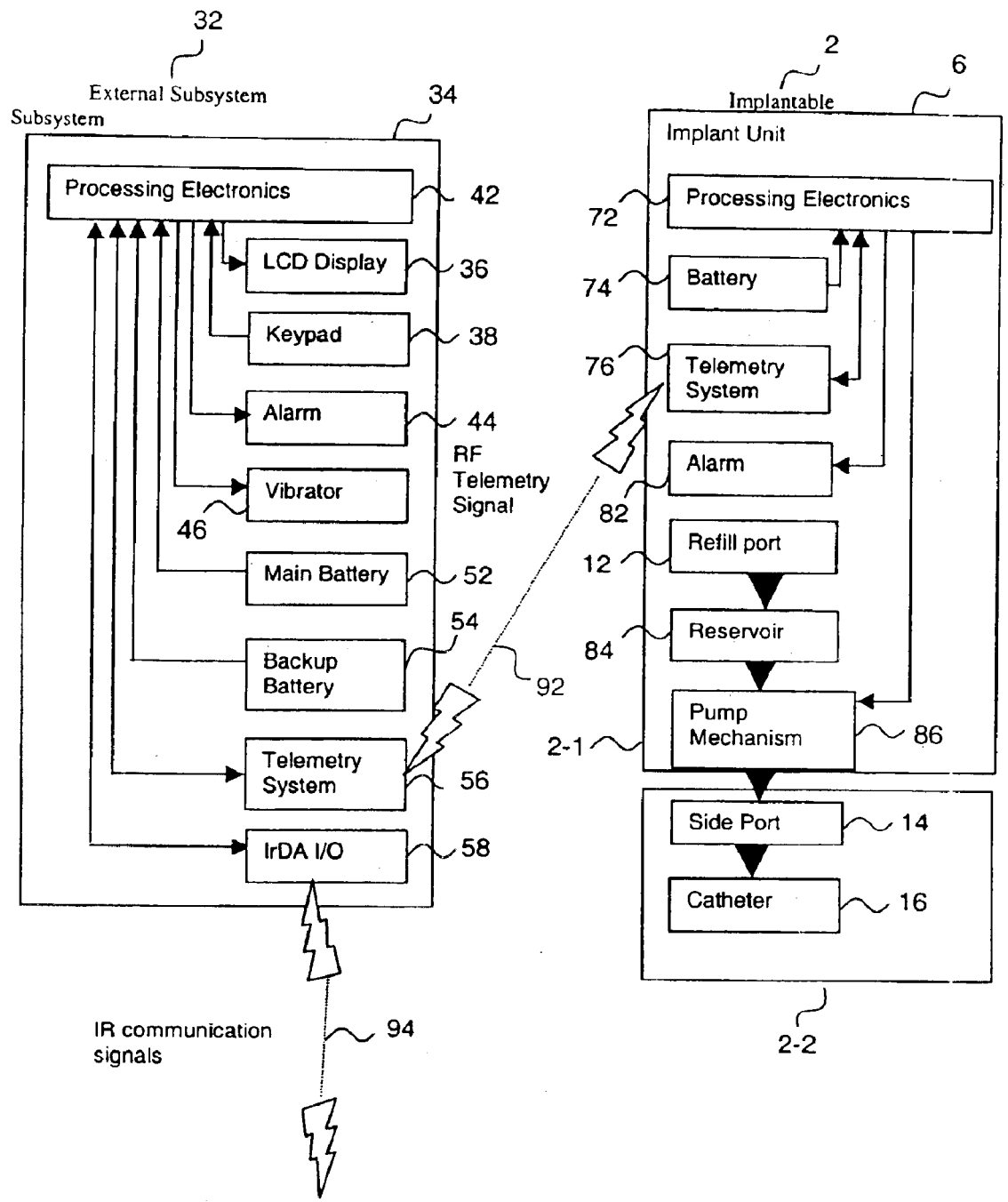
FIG. 3 depicts a block diagram of the main components/modules of both the implantable device and the external communication device of the first preferred embodiment.

FIG. 3 depicts a simplified block diagram of various functional components or modules (i.e. single components or groups of components) included in the implantable medical device 2 and external communication device 32. The external communication device 32 includes (1) a housing or cover 34 preferably formed from a durable plastic material, (2) processing electronics 42 including a CPU and memory elements for storing control programs and operation data, (3) an LCD display 36 for providing operation for information to the user, (4) a keypad 38 for taking input from the user, (5) an audio alarm 44 for providing information to the user, (6) a vibrator 46 for providing information to the user, (7) a main battery 52 for supplying power to the device, (8) a backup battery 54 to provide memory maintenance for the device, (9) a radio frequency (RF) telemetry system 56 for sending signals to the implantable medical device and for receiving signals from the implantable medical device, and (10) an infrared (IR) input/output system 58 for communicating with a second external device.

The second external device may include input, display and programming capabilities. The second device may include a personal computer operating specialized software. The computer may be used to manipulate the data retrieved from the communication device or the medical device or it may be used to program new parameters into the communication device or directly into the medical device, or even used to download new software to the communication device or to the medical device. The manipulation of the data may be used in generating graphical displays of the data to help aid in the interpretation of the data. Such data interpretation might be particularly useful if the medical device provides data concerning a physiological parameter of the body of the patient, such as a glucose level versus time. More particularly the computing power and display attributes of the second device might be even more useful when the medical device includes both an implanted sensor (e.g. glucose sensor), or external sensor, and an implanted pump (e.g. insulin pump), or external pump, where the second external device may be used to enhance the ability to ascertain the effectiveness of the two devices working together. Successful control periods and problem control periods could be more readily identified. In fact, if the two devices work on a closed loop basis or semi-closed loop basis, the analysis performable by the second external device may be useful in deriving new closed loop control parameters and/or in programming those parameters directly into the communication device or the medical device or devices.

The implantable device 2 includes (1) a housing or cover 6 preferably made of titanium that may or may not be coated to enhance biocompatibility, (2) processing electronics 72 including two CPUs and memory elements for storing control programs and operation data, (3) battery 74 for providing power to the system, (4) RF telemetry system 76 for sending communication signals (i.e. messages) to the external device and for receiving communication signals (i.e. messages) from the external device, (5) alarm or buzzer 82 for providing feedback to the user, (6) refill port 12 for accepting a new supply of drug as needed, (7) reservoir 84 for storing a drug for future infusion, (8) pumping mechanism 86 for forcing selected quantities of drug from the reservoir through the catheter to the body of the patient, (9) sideport 14 for providing a replaceable connection between the (10) catheter and the pump housing and for allowing diagnostic testing of the fluid handling system to occur, and catheter 16 for carrying medication from the implant location to the desired infusion location.

In this embodiment, the pump mechanism is preferably a low power, electromagnetically driven piston pump. Such as for example Model Nos. P650005 or P650009 as sold by Wilson Greatbatch Ltd. of Clarence, N.Y. which have stroke volumes of 0.5 microliters and draw under 7 mJ (e.g. about 6 mJ) per pump stroke and under 4 mJ (e.g. about 3 mJ) per pump stroke, respectively. The pump mechanism dispenses a sufficiently small volume of insulin per stroke so that a desired level of infusion resolution is achieved. For example if an infusion resolution of 0.2 units of insulin were desired when using U400 insulin, then a stroke volume of about 0.5 microliters would be appropriate. In other embodiments other types of infusion pumps may be used, e.g. peristaltic pumps.

As depicted in FIG. 3, the implantable device includes a reservoir 84 for holding a desired quantity of insulin. In this embodiment, the drug held in the reservoir is preferably maintained at a slight negative differential pressure (with respect to the pressure on the outside of the housing) so that in the event of a leakage in the reservoir 84 or housing 6, the drug will not be forced from the housing into the body of the patient. The drug is added to the reservoir 84 by means of a transcutaneous needle that is passed from a position exterior to the body into self sealing refill port 12. Due to the slight negative pressure that the reservoir experiences, insulin in a syringe connected to the needled is drawn into the reservoir without need of external force. The drug is extracted from the reservoir 84 and forced through catheter 16 by an electronically controlled pump mechanism 86. In alternative embodiment positive pressure reservoirs may be used in combination with pumping mechanisms that force the medication or drug from the implantable device and/or used with flow restrictors that dispensed the drug at a fixed rate or at a variable rate with the aid of valves or flow diverters.

The size of the reservoir is preferably large enough to hold sufficient insulin so that refilling does not have to occur too often. For example, it is preferred that time between refills be within the range of 1.5–4 months or longer, more preferably at least 2 months, and most preferably at least 3 months. Opposing the containment of a large volume of insulin, is the desire to keep the implantable device as small as possible. In the present embodiment the implantable device and reservoir has been designed to hold about 13 ml of insulin. A preferred insulin has a concentration of 400 units per milliliter and is available from Aventis HOE 21Ph U-400 from Aventis Pharma (formerly Hoechst Marion Roussel AG, of Frankfurt am Main, Germany). This insulin is a highly purified, semi-synthetic human insulin with 0.2% phenol as a preserving agent, glycerol as an isotonic component, TRIS as a buffer, plus zinc and Genopal® as stabilizing agents. This quantity and insulin concentration allows about 2–4 months between refills. In other embodiments higher insulin concentrations may be used (e.g. U-500 or U-1000) to increase time between refills or to allow reduction in reservoir size. In some embodiments, when higher concentrations are used, any quantized minimum delivery amounts may be reduced by modifying the pumping mechanism, control circuitry, or software control algorithm so that infusion resolution is not adversely impacted.

The external communication device contains appropriate software to provide proper control of the device including appropriate functionality to allow communication with the medical device, to allow adequate control of the operation of the medical device, and to give appropriate feedback to the user regarding overall system operation. The medical device is provided with appropriate software to allow communication with the external communication device, to allow safe and appropriate operation of the medical functionality of the device, and to allow direct feedback to the user concerning device status via the internal alarm.

The control electronics of both the implantable device and external communication device are centered around microprocessor based integrated circuits, i.e. processor ICs, that are implemented in the present embodiment in the form of application specific integrated circuits (ASICs). In the present embodiment, the control electronics of the implantable device are centered around two identical ASICs that are mounted on a hybrid circuit board. In some alternative embodiments a single ASIC may be used, or a single dual processor integrated ASIC may be used. In a single processor device one or more circuits may be provided to monitor the operation of a CPU in the processor to ensure it continues to operate properly in one or more key functions. In the single dual processor integrated ASIC, dual circuitry would be provided so that each processor could act independently of the other. In the single dual processor embodiment, a single off-circuit oscillator may be used to drive both processors or each may have an independent oscillator. A single chain of timing circuits could be used in driving both processors or independent chains of timing circuits could be used. Furthermore, if a single oscillator is used to drive both processors, then one or more separate circuits such as a counter and an RC timer may be used to verify appropriate operation of the oscillator and/or any particular timing circuit dependent thereon.

In different embodiments, more or less of the control electronics may be implemented within one or more processor ICs while any remaining portions may be implemented external to the processor ICs. The processor IC may be referred to as an MD processor if used in the medical device portion of the system or a CD processor if used in the communication device portion of the system. In other embodiments the process IC used in the communication device may be different, e.g. have a different CPU or different peripheral modules, from a processor IC used in the medical device. In embodiments where more than one processor IC is used in either the medical device or the communication device each of the processors may be different. They may be specifically designed for their intended roles when they perform at least partially different functions. Depending on particular design constraints portions of the electronics not embodied in the processor ICs may form part of one or more hybrid circuit boards or be otherwise mounted within, on, or even in some cases external to a device housing.

Each processor IC of the present embodiment includes a 16-bit core CPU which is a CMOS low power version of the INTEL 8086 processor and various peripheral modules that are used for system control, data acquisition, and interfacing with electrical components external to the processor IC.

The peripheral modules of the processor IC include (1) a non-volatile memory interface module, e.g. a SEEPROM interface module, (2) a boot ROM module; (3) an SRAM module; (4) a memory decoder module; (5) a crystal oscillator module; (6) a timer module; (7) a pump interface module; (8) a watchdog module; (9) an RF module; (10) an interrupt handler module; (12) an analog-to-digital converter module; (13) an LCD clock driver module; (14) an alarm interface module; and (15) first and second synchronous serial interface modules.

In alternative embodiments fewer, additional, or different peripheral modules may be incorporated into the processor ICs. In one extreme the processor IC may simply incorporate a CPU with all other modules being external thereto. In the other extreme almost all, if not all, electronic components may be incorporated into a single processor IC. Intermediate alternatives might incorporate a single additional module into the processor IC (in addition to the CPU), others might incorporate more than one, e.g. 4 or more, 8 or more, or the like. In still other alternatives, the number of peripheral modules or components in an entire device may be considered and more than a certain percentage of them incorporated into one or more processor ICs, e.g. more than 50%, more than 75%, or even more than 90%.

The processor ICs are responsible for basic system management and communication of information between the implantable device and the external communication device through the RF telemetry link. The telemetry systems of the present embodiment are implemented in part through electrical hardware and in part through software controlled by a processor IC.

In the present embodiment, most of the required electrical modules for the implantable device are integrated within the processor ICs. However, several are not. These additional modules include two independent crystal oscillators (one for each ASIC); two non-volatile memory modules (one for each ASIC), e.g. SEEPROM chips; a volatile memory module (used only by one of the ASICS), e.g. an SRAM chip; pump driver circuitry (partially controlled by the each ASIC); front end telemetry system circuitry; and voltage measurement circuitry associated with the pump driver circuit; a buzzer; and a battery.

Within the implantable device telemetry operations are controlled by a single ASIC (sometimes known as the main processor) The other processor (sometimes known as the monitor processor) controls the buzzer and is thus responsible for audio communications coming from the implantable device. The medical functionality of the implantable device (i.e. the administration of insulin in the present embodiment) is controlled by both processors. To maintain the implantable device in a fail safe operational mode, these two processors maintain an appropriate level of agreement concerning infusion instructions an error condition results and either pumping is halted or a system reset may be made to occur. The main and monitor processors communicate with each other through the use of hardwired serial input and output ports.

As with the implantable device, the control electronics of the external communication device are centered around an ASIC that controls and interacts with a number of peripheral modules. These peripheral modules include an LCD display and driver, an IR port and driver, a crystal oscillator, a keypad and keypad interface, power management modules and reset circuitry, external volatile memory (e.g. SRAM) and non-volatile memory (e.g. SEEPROM), a buzzer, and front end telemetry hardware.

The telemetry system for the implantable device and the external communication device provide a half-duplex link between each other using a carrier frequency of about 250 kHz (e.g. about $2^{18}$ Hz) and a data signal having a frequency of about 8 kHz (e.g. about $2^{13}$). The transmitter hardware uses the 8 kHz data signal to modulate the carrier signal to generate signals that will be transmitted by the antenna. The receiver hardware receives the modulated signal and demodulates it to extract the 8 kHz data signal. Both the implantable device and the external communication device have transmit and receive capabilities to allow two-way communication.

Most of the RF telemetry circuits necessary for communication between the external communication device and the implantable device are implemented in the processor IC. In order to minimize the digital noise interference that the processor IC might impart to the weak RF signals that are being received, a high-gain RF amplifier is implemented off-chip. Also an RF antenna, that is used for both transmission and reception, and circuitry to select between reception and transmission are implemented off-chip. The remaining analog sections and all the digital demodulation circuits are implemented in the processor IC.

The RF module of the processor IC outputs in phase and quadrature phase signal components for combined transmission by the external antenna. The RF module also supplies a control signal that is used to switch between a transmission configuration and a reception configuration. The RF module receives as inputs signals from the amplification circuitry.

A Quadrature Fast Acquisition Spread Spectrum Technique (QFAST®) is used as the modulation technique. QFAST® modulation is based on an Offset Quadrature Phase Shift Keying (QPSK) modulation technique. In this technique, data generated by the CPU modulates clock signals at the carrier frequency. As a result of quadrature modulation, in-phase and quadrature-phase components of the given data stream are generated. The two components are then applied to opposite ends of the external antenna so that a combined signal is transmitted.

As noted above, external to the processor IC, the received RF signal is amplified by a high gain receive amplifier. A bandpass filter is used to attenuate out-of-band components such as those due to AM radio stations. The amplified RF signal then enters a mixer in the RF module of the processor IC and is converted to baseband using two mixers, one in-phase mixer and one quadrature phase mixer both at the carrier frequency. The mixer outputs are the quadrature components of the baseband signals. An integrator & dump function in the RF module then removes the sum frequency (2 fc) and high frequency noise (i.e. acting as a low pass filter) from each of the two signals. The processed signals are then digitized using a comparator and passed to the demodulator where the data and clock are recovered.

In QFAST®, data rate adaptability is accomplished through a spread-spectrum "coding gain" concept, with the spreading code being a simple clock. The modulation produced by the QFAST® modulator is demodulated in a manner which delivers both clock and data. All of the QFAST® modulation and demodulation circuits are digital and are incorporated into the processor IC.

The QFAST® technique provides a communication system with a number of attributes: (1) it extracts the clock from the received signal without a clock recovery loop; (2) it provides demodulation of data without phase ambiguity and without the requirement for synchronous demodulation; (3) it makes effective use of the available transmission bandwidth, (4) it results in fast acquisition of the message signal; (5) it is relatively immune to the effects of highly dispersive and distorting propagation media; (6) it does not require regeneration of a phase-coherent local replica at the receiver of the transmitted carrier; (7) it does not require resolution of ambiguity between the in-phase and quadrature-phase channels in the receiver; and (8) it does not exhibit data phase ambiguity.

Further detail about QFAST® (Quadrature Fast Acquisition Spread Spectrum Technique) may be found in U.S. Pat. No. 5,559,828, entitled Transmitted Reference Spread Spectrum Communication Using a Single Carrier with Two Mutually Orthogonal Modulated Basis Vectors, by Armstrong, et al.

The RF module in the processor IC consists of timing circuitry, circuitry to maintain time synchronization between the implantable device and the external communication device, a digital RF transmitter section that includes a QFAST® RF modulation transmitter, an analog receive module, and a digital receive section that includes a QFAST® RF modulation receiver.

Further details about the structural and functional configuration and operation of preferred ambulatory medical devices and preferred communication devices are found in several U.S. patent applications.

The RF communication between the implantable device and the external communication device occurs in the form of messages (sometimes referred to as communication signals or packets) that are passed back and forth between the two devices. In this embodiment these messages have a multi-part format or protocol: (1) preamble, (2) frame sync, (3) telemetry identifier, and (4) data.

In other embodiments other multipart formats may be used. For example, the multipart format might consist of (1) a preamble, (2) a telemetry identifier, and (3) data. In still other embodiments the preamble and frame sync may be combined into a single entity, or the telemetry identifier and the frame synch may be combined into a single entity, or even all of the preamble, frame sync, and telemetry identifier may be combined into a single entity such that the functionality of associated with these individual elements of the messages of the present embodiment may be performed simultaneously or in series based on a single but repeated pattern of information.

For communications from the implantable device to the external communication device the preamble is a repeating pattern of "10", i.e. 10101010. This alternating pattern of ones and zeros is broadcast for 8-bit times. This pattern is considered the standard preamble pattern. In other embodiments this standard preamble pattern may be different from that noted above (e.g. it may be a repeated pattern of "01" instead of "10"). Though, unnecessary, the standard preamble need not transition with every other bit though, as a certain number of bit transitions are typically necessary to establish bit synchronization, the more transitions, the shorter the minimum length that the preamble can take.

For communications from the external communication device to the implantable device, the preamble is either of the standard preamble pattern but applied for an extended number of bit times (e.g. 24, 48, or 96) or is of an attention preamble pattern that is applied for, typically, even a longer extended number of bit times. In other embodiments, not only may the preamble used by the implantable device and the external communication device have different lengths as used in this embodiment, they may also use different standard preamble bit patterns. Of course in still other embodiments, a same preamble length may be used by both the implantable device and the external communication device whether or not the same standard preamble bit pattern is used. The attention preamble pattern is formed of a repeated pattern of "110110 . . . 110". In other embodiments, other attention preamble patterns may be used (e.g. repetitions of "011", "100", "001, "1011", and the like).

The preamble, whether of the standard pattern or the attention pattern, is used so that the RF reception hardware can establish bit synchronization (i.e. bit boundary recognition) of the incoming data. However, the attention preamble is further used to get and hold the receiver's attention for a defined period of time. As long as the attention preamble is being received, the receiver's hardware will stay on and continue tracking the signal in anticipation of an incoming message. In other embodiments, the concept of a standard preamble pattern that will not hold the receiver's attention may be dispensed with in favor of always using a preamble that is in effect an attention preamble.

The attention preamble is considered to be lost, or no longer being received, when the receiver receives more than 2 inappropriate bit values during receipt of any 64-bits or when the frame sync pattern is received.

Before beginning error detection, the receiver's hardware first requires that the receipt of the attention preamble be established. In establishing receipt of the attention preamble the receiver's hardware may load the received bits into a shift register and may then compare the shifting pattern to a predefined pattern of selected length and then may consider the receipt of the attention preamble to be established once the comparison indicates a match of sufficient length has occurred. The receive hardware then continues to compare received bits to predicted bits based on the pattern established. A bit counter is incremented with each bit received and an error counter is incremented with each error detected. The bit counter is reset whenever an error is detected. The error counter is reset whenever the bit counter reach a preset value. If the error counter should reach a predefined error amount, the established attention preamble is considered to have been lost and if the receiver is still operating within its listening period, the receiver's hardware continues its process of trying to establish receipt of attention preamble. The parameters associated with establishing receipt of the attention preamble and associated with the setting of error tolerances may be hardcoded into the system or they may be programmable into hardware registers.

It is preferred that the above analysis be implemented in hardware due to the energy savings possible but in other embodiments the process may be implemented via software.

Of course in other embodiments, the error tolerance believed acceptable may be increased or decreased or defined in a different manner. For example, instead of using an error tolerance of 2-bits out of 64-bits, one might use a tolerance of 1/32. The tolerance may even be increased to 2/32, 3/64, 4/64, or even higher. Alternatively, it may be decreased to 1/64, 1/128 or even to zero.

The attention preamble may be used when there is some uncertainty in the time synchronization of the two devices. The extra length of the attention preamble allows the receiver's reception window to open a little later than anticipated and to still have the receiver pick up the entire message. The extra length of the attention preamble allows the receiver's reception window to open earlier than anticipated, so long as a minimum number of bits are heard by the receiver during the time its reception window is normally open, and still have the receiver's attention locked onto the preamble and have the receiver remain on as long as the attention preamble is being received, plus a little more, in anticipation of receiving a frame sync pattern.

The receiver may miss some of the initial bits in the preamble but a minimum number of bit transitions (e.g. 4, 6, or 8 transitions) of the preamble pattern must be received to ensure bit synchronization between the transmitted message and the receiver. In the present embodiment, the implantable device broadcasts with a minimal preamble size in order to reduce power consumption within the implantable device. In other embodiments, the preamble used by the implantable device may be larger relative to the minimum number of bit transitions needed to establish bit synchronization.

In the present embodiment, frame sync may actually be considered byte sync (i.e. frames are bytes) and is a single byte of a selected pattern and is used so the receiver can obtain byte boundaries for the transmitted data. In the present embodiment, the selected pattern is "10110000". In other embodiments, other patterns, pattern lengths, and frame sizes may also be acceptable for use as frame sync so long as the patterns (in combination with preamble or attention preamble patterns and any tolerances in their reception) cannot lead to errors in defining byte transitions. In still other embodiments, the attention preamble pattern may be of the same bit pattern as the frame sync, in which case, some error tolerance may be allowed in the frame sync pattern and the receiver's attention would be held until the pattern is lost or a valid telemetry ID pattern is received. This latter alternative requires that various potential telemetry IDs be disallowed.

Even during the receipt of attention preamble (or other preamble) the receiver continually compares shifting bits that are received to the anticipated frame sync pattern. The Frame Sync byte may be detected by feeding the incoming bit stream into a shift register and passing the bit values in the register to the inputs of an 8 input AND gate whose input assertion levels correspond to the anticipated frame sync pattern.

This comparison process continues so long as the receiver continues to listen for an incoming message or until a valid frame sync pattern has been received. If the receiver is continuing to listen beyond its normal reception window (i.e. listening period), due to the reception of an attention preamble, the listening will not stop immediately upon the attention preamble being lost. The comparison process for ascertaining the receipt of frame sync continues for a number of bits after attention preamble is lost, even if the listening period has ended, as its loss may be associated with the partial receipt of frame sync. Once frame sync is received a valid frame sync signal is asserted.

In the present embodiment, the telemetry identifier (i.e. telemetry ID) is a 3-byte value that is used to ensure that only the intended receiver receives a message. The value of all "1s" indicates a universal message that is to be received by all receivers, otherwise the telemetry ID must be agreed upon between the receiver and transmitter. A unique ID is provided for each implantable device and each external communication device during manufacturing. Only the external communication device can transmit a message using the universal ID code. The telemetry IDs that the receiver will consider to be valid are the ID of the receiver or the universal ID. All other incoming bit patterns will be rejected with the result that the receiver will be either turned off or will start again looking for a valid frame sync pattern attention preamble. In alternative embodiments, instead of the receiver accepting only its own ID (in addition to the universal ID) it may instead accept the ID of the transmitter. In other alternative embodiments, a different length preamble may be used by the implantable device and the external communication device. In still further alternatives, the telemetry IDs may not be unique if it is believed that the chance of miscommunication between devices is not a significant risk. In fact, if there is little risk of miscommunication, telemetry ID may be dropped from the message protocol.

Other embodiments may retain the concept of telemetry ID for either the receiver or the transmitter or both but only pass the telemetry ID information implicitly. Such implicit transfer might use the telemetry ID information in generating a validation code (e.g. CRC) that is transferred with the message. In such cases the receiver could compare the received code to one or more different codes generated using each of the unique telemetry ID and the universal telemetry ID. These embodiments would be less preferred when power consumption considerations are critical, as the telemetry system of the receiver would have to remain on to receive the entire message in order to determine whether the message was for it or not.

After a Frame Sync byte is detected, the processor IC hardware compares the next 24 bits of the incoming data to the personal ID bits and to the universal ID which in this embodiment is fixed at 0xFFFFFF. If a valid telemetry ID is received, the receiver listens to the remaining portion of the message. If a valid telemetry ID is not received listening by the receiver may be aborted, if the listening period has expired, or listening for attention preamble and frame sync may continue, if the listening period has not yet expired.

In alternative embodiments the frame sync and telemetry ID may be combined into a single entity that is identified as a whole as opposed to the present embodiment where the two pieces are looked for and identified separately.

In the present embodiment, data is provided in an integer number of bytes following the telemetry ID. In the present embodiment the first byte of the data indicates the message type. The first seven bits of the first byte is an operation code or op-code while the eighth bit is either ignored or is set and interpreted as a sequence number (to be discussed hereafter) dependent on whether or not the first seven bits call for a sequence number or not. Each op-code, based on its nature, is followed by data in a defined number of bytes. The specific op-code itself may dictate the number of bytes that follow or alternatively the specific op-code may dictate that the number of bytes to follow may be extracted from the first byte or several bytes of information that follow it. In alternative embodiments, op-codes may have a different length, or not be used at all, the message length or message end may be dictated in other ways. Based on the op-code and potentially one or more bytes following it, the receiver knows exactly how many more bytes of data to listen for. After receiving those bytes, the receiver may be turned off to conserve power.

For some messages dealing with drug delivery, the data portion of the message may include a bolus number. The bolus number is similar to the sequence number in that it is incremented by both the implantable device and external communication device under controlled conditions so as to reduce the possibility of bolus requests being delivered more than once when duplicate requests may be made as a result of the external communication device failing to receive a confirmation that a previous request was received. The bolus number may be a single bit number in some embodiments but in more preferred embodiments it is a multibit number (e.g. 2-bit, 4-bit, 7-bit, 1-byte, or 2-bytes) so that it can take on more than two values thereby making it less likely that an error will escape detection due to received and expected numbers erroneously matching. The incrementing of the bolus number may occur within the external communication device when it receives confirmation that a message was correctly received and it may be incremented by the implantable device when it correctly receives a bolus request. As such when a duplicate request for a bolus is received by the implantable device it can recognize that the expected and received bolus numbers do not match and that requested bolus is not a new request. As such the implantable device can respond to the repeated request that the bolus was correctly received and delivered (with out performing a second delivery and without incrementing its expectation of what the next bolus number will be).

In other embodiments, other incrementing numbers may be used to help ensure that only appropriate operation of the implantable device occurs. For example, incrementing temporary basal rate numbers may be used, and/or separate incrementing numbers may be used for different types of boluses that might be requested, e.g. phase 1 boluses and/or phase 2 boluses. In still further alternatives, incrementing message numbers may be generally used. These message numbers may for example be used on all messages that have responses associated therewith. Once the receiver confirms that a message was appropriately received it may increment its message number. Similarly, once the transmitter gets a response to the message it sent, it may likewise increment its message number.

In the present embodiment, the data portion of the message ends with a one or 2-byte validation or error checking code (its type is dictated by the op-code included with the message). The preferred error checking code of this embodiment is in the form of a cyclic redundancy code (CRC). In other embodiments, the CRC may be replaced with another error checking code and/or it may be placed in a different part of the message or even deleted from the message protocol completely. The op-code may also be placed in another part of the message, or deleted in favor of other techniques that may be used in interpreting the message and for determining when the end of the message has been properly received.

In the present embodiment it is preferred that the CRC occur at the end of the message as it simplifies the computational efficiency of confirming the validity of the message by the receiver. In alternative embodiments, where message compilation and transmission occur in parallel, placing the CRC at the end of the message also allows the data to be processed and transmitted in a single pass without a need to have storage space for the entire message available.

In the present embodiment, the telemetry system may lose bit synchronization if insufficient bit transitions are received per unit time (e.g. if more than about 100 to 120-bit times lapse without receiving a transition. In order to ensure that a sufficient number of bit transitions occur, the data portion of the message, with the exception of the op-code is randomized prior to transmission and is de-randomized upon receipt. In alternative embodiments, at the cost of sending more data, instead of randomizing the data, periodic bytes of data with transitions may be added to the protocol (e.g. after every fifth or tenth byte of data, a byte, or at least two bits, may be transmitted for the purpose of ensuring that a transition occurs so that bit synchronization is maintained). In further alternatives, as short messages may not be subjected to improper reception due to loss of bit synchronization, randomization may be limited to use with longer messages (e.g. messages with data portions longer than 10 to 15-bytes).

In order to keep power requirements low in a preferred implementation, the external communication device and implantable device attempt to maintain a common time base, transmissions are set to start at specified times, and reception windows are set for specified times and lengths. In this way, the receiver may remain in a powered down mode most of the time and can turn on to listen for a potential incoming message at the specified times for the specified lengths of time. If a message is found to be incoming, the receiver stays on, otherwise it goes back to sleep (i.e. power down mode).

In the present application, to avoid ambiguities in some portions of the description relating to the timing associated with the transmission and reception of messages, the following definitions will be used: (1) "inbound" will generally refer to activities associated with telemetry reception by the medical device, whether implanted or not, or to activities associated with telemetry transmission by the communication device, (2) "outbound" will generally refer to activities associated with the telemetry transmission by the medical device, whether implanted or not, or to activities associated with telemetry reception by the communication device.

According to a telemetry timer in the medical device, outbound transmissions begin at an "outbound transmission start time" and continue for an "outbound transmission period" which defines the period that the preamble portion of the message is sent either in terms of time or in terms of the number of data bits. Similarly, according to a telemetry timer in the communication device, inbound transmissions begin at an "inbound transmission start time" and continue for an "inbound transmission period" which defines the period that the preamble portion of the message is sent either in terms of time or in terms of the number of data bits.

Furthermore, according to the telemetry timer in the medical device, the telemetry reception system of the medical device begins listening for messages at an "inbound listening start time" and continues to listen for an "inbound listening period" which may be thought of in terms of a time period or a given number of data bits. Similarly, according to the to the telemetry timer in the communication device, the telemetry reception system of the communication device begins listening for messages at an "outbound listening start time" and continues to listen for an "outbound listening period" which may be thought of in terms of a time period or a given number of data bits. Additionally an "inbound listening interval" may be defined as the interval between the successive inbound listening start times while an "outbound listening interval" may be defined as the interval between the successive outbound listening start times. Throughout the specification, the above timing elements may be referred to in different ways particularly when it is believed that the intended meaning is clear from the context of the description. However, when the precise meaning is required, descriptions will be based on the above definitions so as to remove ambiguity.

In the present protocol, no more than one message can be received for each reception window or listening period. In alternative embodiments, however, a "multiple message op-code" and a "number of messages parameter", or the like, may be used such that the receiver knows that it must remain on until an indicated number of messages have been received.

As noted above, in a preferred implementation of the present embodiment, telemetry hardware is used to identify the bit sync, frame sync, and telemetry ID portions of an incoming message as opposed to using software to interpret the initial bytes of a potential incoming message. After the hardware confirms that the incoming message is for the particular receiver, the hardware activates the CPU of the processor IC so that software can aid in receiving, interpreting, and validating the message. This allows the power consumption of the receiver to remain at a minimum level while waiting for incoming messages to be initially screened. Also as noted above, in a preferred implementation the receiver only listens for incoming messages at discreet intervals for limited periods so as to further minimize power consumption associated with maintaining communication. As it is preferred that the limited listening periods are relatively small compared to the listening intervals, it is preferred that a reasonable level of time synchronization be maintained between the transmitter and receiver so as to minimize excess power consumption and user inconvenience associated with using extended attention preambles, multiple communication attempts, or the like, to ensure appropriate information transfer is achieved.

In alternative embodiments, particularly where power consumption is less critical, the power of the microprocessor might be utilized to control the telemetry hardware during the reception of any or all of the preamble, frame sync, or telemetry ID portions of the message or may even be used to activate the reception hardware at the listening start time and to deactivate the hardware at the end of the listening period if it is determined that no message was incoming.

In a preferred time synchronization implementation, the concept of time at the second and subsecond level is dictated by the implantable device, whereas the concept of time at the minute and hour level is dictated by the external communication device. Of course, other synchronization schemes may be alternatively defined.

In the present embodiment, transmissions are allowed to begin only at the beginning of a second as measured by the transmitter's telemetry timer. Selected seconds boundaries within each minute are assigned either as a potential outbound transmission start time from the implantable device to the external communication device or as a potential inbound transmission start time from the external communication device to the implantable device (e.g. each even second mark may represent a potential start time for inbound transmissions, while one or more odd second marks during each minute represent potential start times for unsolicited outbound transmissions. A predefined inbound transmission start time may be replaced by transmission start time for a solicited outbound message as the external communication device is awaiting a response to the communication device solicited the response from the implantable device. In other embodiments, potential transmission times may be set to start on something other than boundaries of seconds. In still other embodiments, the external communication device may continue to transmit messages based on inbound transmission start times as the implantable device may be listening only during predefined inbound listening periods, while the implantable device may be able to transmit at any time, outside of its normal predefined listening time slots, as the external communication device may be continuously listening for outbound communications any time it is not transmitting, or setting its outbound listening interval to a small value (e.g. a opening of its reception window for small periods every few milliseconds) to see if any messages are incoming. This may be acceptable as power consumption in the external communication device is less critical than in the implantable device.

In the present embodiment, depending on the type of message, a 1-byte or 2-byte cyclical redundancy code (CRC) follows the data bytes. It is preferred that the CRC be generally computed using the telemetry ID of the message originator (i.e. the telemetry ID of the transmitter). This serves as a form of security. If a message with this type of CRC is received by an implantable device, the implantable device must have advanced knowledge of the telemetry ID of the transmitting external communication device or the implantable device will reject the message because of a CRC error. Similarly the communication device may simply reject messages that do not originate from its partnered medical device.

A CRC to be included with a message, in the present embodiment, is calculated based on the successive bytes forming the message and possibly upon the identity of the transmitter as well. When the CRC is computed using the telemetry ID of the message originator, the first three bytes used in the calculation are the telemetry ID of the originator. The CRC calculation then uses the three bytes of the telemetry ID of the intended receiver, the 1-byte of op-code, and then the remaining bytes of data in the message (with the exception of the CRC itself that is being calculated). When the CRC is not computed with the message originator's Is telemetry ID, the CRC is computed based on the bytes of the message starting with the message op-code, and continuing with the rest of the bytes in the data (with the exception of the CRC itself that is being calculated). Of course, in other embodiments, the CRC calculations may use the telemetry ID of the originator other than at the beginning of the calculation. In still other embodiments, the op-code may be left out of the CRC calculation. In still other embodiments, the order in which the components of the messages are calculated may be changed, though if different from the order presented in the message itself, recalculation of the CRC by the receiver may not be able to be performed on the fly as the message is being received as is done in the current embodiment.

In the present embodiment, it is preferred that a precalculated CRC transmission key and a precalculated CRC reception key are derived and stored so that they do not have to be calculated each time they are needed. The transmission key is a CRC derived from the byte-by-byte processing of the transmitter's three byte telemetry ID followed by the receiver's three byte telemetry ID. The reception transmission key is a CRC derived from the byte-by-byte processing of the transmitter's three byte telemetry ID followed by the receiver's three byte telemetry ID. Though these key definitions sound the same it must be remembered that the transmitting and receiving roles and devices are reversed. These keys are used as the starting points for deriving the CRC that is to be transmitted with the message and the CRC that is derived upon receipt of a message, respectively. In other embodiments other keys may be defined.

Further details about CRC generation may be found in (1) above referenced concurrently filed U.S. patent application Ser. No. 09/768,221, (2) the "CCITT Red Book", Volume VIII, published by International Telecommunications Union, Geneva, 1986, Recommendation V.41, "Code-independent Error Control System", and (3) "C Programmer's Guide to Serial Communications", 2nd Edition, by Joe Campbell, published by SAMS Publishing, Indianapolis, Ind., ISBN 0-672-30286-1. In particular chapter 3 of this latter book deals with errors and error detection including CRCs, while chapter 23 deals with calculation of CRCs. These books are hereby incorporated by reference herein as if set forth in full.

In a preferred implementation, the clock in the implantable device is the master clock in terms of tracking seconds within a minute and subseconds within a second. The implantable device obtains its concept of the minute number within an hour and hour within a day from the values set in the external communication device which typically correspond to the time of day at the patient's location. The values for subseconds within a second are preferably transmitted implicitly by the implantable device to the external communication device based on the implicit understanding that implantable device transmissions always start at second boundaries.

More specifically, each time the external communication device receives a transmission from the implantable device, it uses a combination of elements to calculate a difference between the external communication device clock and the implantable device clock. These elements include (1) the exact time that a certain portion of the transmission is received according to the external communication device clock, (2) knowledge that implantable device message transmission begins a known time according to the implantable device's clock, and (3) a known time difference between that portion of the transmission and the beginning of the transmission. These three elements may be used to determine any difference in time between the clocks and ultimately to resynchronize the clocks. Of course, in alternative embodiments synchronization may be implemented in other various ways.

In a preferred implementation, telemetry transmission and reception time slots begin exactly at one-second boundaries. Some time slots are unassigned while others are assigned as slots for communications that are inbound to the implantable device. During normal operation each even second, relative to the minute mark, is slotted for inbound transmissions. In a storage mode, the 0, 15, 30, and 45 second marks are slotted for inbound communications. Storage mode is a state of the implantable device where power consumption is reduced to a minimum level during periods of non-use thereby conserving battery power and thus extending the life of the implantable device. The one second mark after the roll over of each minute is assigned as a slot for unsolicited outbound messages (i.e. messages that are sent without a triggering message from the external communication device). Messages sent from the implantable device in response to external communication device communications (i.e. solicited messages) are sent out on the next available second mark. In alternative embodiments, it is apparent that other inbound and outbound slots may be defined.

Since most system communications of the present embodiment originate with the external communication device, and as a rapid response to programming commands is desired for user convenience, it is preferred that inbound slots be placed relatively close together (e.g. no more than 15 seconds apart, more preferably no more than 10 seconds apart, and even more preferably no more than 5 seconds apart, and most preferably no more than about 2 seconds apart. In order to save battery power on the implantable device, it is generally preferred that the system have relative few outbound slots so that the implantable device doesn't consume excessive power when unsolicited messages from the implantable device are not often used. In general, it is preferred that there be more predefined inbound time slots per time period than outbound time slots. Of course in alternative embodiments outbound time slots may exceed or equal the number of inbound time slots.

When the external communication device sends an inbound message that requires a response, the external communication device listens for the anticipated response from the implantable device that will be sent out on the next one second boundary. If a response is not received in a predefined period of time, the external communication device may automatically retransmit the message one or more times prior to alerting the patient of a failure to communicate.

In the present embodiment, all transmissions both inbound and outbound, and both solicited and unsolicited are sent using the same data transmission rates and the same carrier frequency. In alternative embodiments, however, data transmission rates may be varied, and carrier frequency may be varied. Such variations may be based on predefined time slot definitions so that both the implantable device and external communication device may properly vary their reception parameters in anticipation of how the other device may attempt to communicate. For example, solicited transmissions may occur at a different carrier than unsolicited transmissions or may occur using a different data transmission rate. The external communication device may transmit on inbound time slots with a first carrier frequency and first data rate, and the implantable device may transmit on outbound time slots with a second frequency or second data rate that may be different from the first frequency or first data rate. In still further embodiments, transmission reception & frequency may be user selectable if communication problems are excessive in the hope of finding a frequency with less interference.

To reduce power consumption, it is desirable to have telemetry hardware operate only during actual transmission times and during possible reception times and to have the CPU off for a large portion of the possible reception times and for a large portion of actual transaction times. As such, the hardware, as discussed above, is configured and controlled so that this result is achieved. As power conservation in the implantable device is more critical than power conservation in the external communication device, this first embodiment places the burden associated with synchronization activities and activities associated with reestablishing synchronization, once it is lost, onto the external communication device. This desire to minimize power drain in the implantable device is balanced with a desire to have the implantable device respond quickly to commands transmitted by the external communication device. Once a command is issued by the external communication device, it is preferred, for user/patient convenience, that the implantable device receive and acknowledge the command as quickly as possible. To this end, the implantable device is provided with closely spaced reception slots (i.e. inbound listening intervals, e.g. every 2 seconds) so that communication can occur with a sufficiently fast response. Each inbound listening period, however, is of very short duration so that power consumption in the implantable device is minimized.

The duration of each inbound listening period is preferably not so small that slight variations in synchronization cause lost of reception, which would cause a delay in communication, as well as potentially causing extra power consumption in order to reestablish communication as the reception hardware may be forced to remain on for extended periods of time due to the reception of lengthy attention preambles. As such, in the present embodiment the reception time slots are turned on for an initial period of about 2–8 milliseconds (e.g. 4 milliseconds) while using an 8 kHz data transmission rate with a minimum number of 8-bit transitions necessary for establishing bit synchronization.

In alternative embodiments longer or shorter windows may be used. Relative to the incoming bit rate, it is preferred that the window remain open in the range of about one and one-half to four times the period necessary to establish bit sync and receive a complete frame sync signal.

In other alternative embodiments, if attention preamble is sent, the window may be opened only for a period necessary to establish receipt of the attention preamble and thereafter, frame sync and a valid telemetry ID may be looked for. In this alternative, to enhance likelihood of reception, the transmitter preferably does not begin transmission at what it believes is the most likely time that the receiver begins listening, but instead begins transmission at a somewhat earlier time with an attention preamble of sufficient length to cover or at least sufficiently overlap the anticipated listening period.

In the present embodiment, the implantable device always starts a transmission exactly at (an outbound transmission start time which corresponds to a second boundary) according to its own clock. The external communication device may activate its receiver at what it believes is the implantable device's outbound transmission start time based on use of any synchronization parameters established in conjunction with the previous communication(s). The external communication device may leave its reception window open for a predefined minimum period of time or alternatively it may adjust the listening period based on one or more parameters. The receiver may use one or more additional parameters to adjust the opening of the reception window to somewhat earlier than what it believes the actual start of the potential transmission is to be. This early opening of the reception window may be based on an anticipation that a certain amount of increasing uncertainty exists in the validity of the previously established synchronization and associated previously established drift parameters. In other words, this may be done in recognition that there is a tolerance around which synchronization may be drifting. Such additional parameters may also be used to lengthen the reception window beyond a predefined initial listening period.

In this embodiment, the implantable device always turns on its receiver exactly at the beginning of an inbound reception time slot. As such, if the external communication device has a message to transmit to the implantable device during that reception time slot, the external communication device may start transmitting at what it believes is the beginning of the time slot based on an estimated amount of drift that may have occurred. Alternatively, it may begin transmitting somewhat ahead of its best estimate as to when the time slot will open, in anticipation that there is some degree of uncertainty in the actual amount of drift that has occurred between its measure of time and that of the Implantable Device. In this regard, the external communication device may use an extended preamble, possibly of the standard pattern if not extended too long, but more preferably of the attention pattern so the chance of establishing communication is increased due to the receiver's attribute of having its attention held (i.e. reception hardware retained in an active state) by a communication that consists of the attention preamble pattern. The parameter used in causing the window to open early may be a fixed parameter, or a parameter that is based, at least in part, on the time difference between the present time and the time of last establishing synchronization and possibly based on an estimate of maximum likely drift rate or based on an actual amount of drift experienced between the last two communications or between several communication or associated with an amount or amounts of drift experienced during approximately the same time periods during one or more previous days. Similarly, the parameter used to extend the length of the standard preamble or attention preamble, or even to select between them, may be a fixed parameter, a parameter that is based, at least in part, on the time difference between the present time and the time of last establishing synchronization or a parameter with a different basis.

If it is determined that resynchronization is needed, the external communication device may establish re-synchronization in one of several ways. The external communication device may transmit a message with an extended preamble consisting of the attention preamble. This process may be done as a single step or it may be done in multiple steps. In the single step process, the attention preamble is set to a length of time equal to or somewhat greater than the length of time between inbound listening intervals. This message is preferably a sync message as will be discussed hereafter though it may be also be a different message. After transmission of the message, the external communication device leaves its receiver open for at least about 1–2 seconds in anticipation of the implantable device sending an outbound response. The timing of the sync response message, as well as its content, will provide the information necessary to reestablish synchronization.

The sync message is preferred over other messages because other messages may not carry as much information about timing between the implantable device and the external communication device as is carried by the sync message. For example, all response messages may be used to reestablish synchronization of the second boundaries, but not all messages necessarily carry sufficient information to reestablish even versus odd second boundaries or information necessary to reestablish one-minute boundaries.

In one variation of this one step process, the external communication device begins transmission of the message somewhat after its best estimate (if it has one) as to when the reception window on the implantable device will be closing. In this variation, it is hoped that the implantable device's receiver will open its reception window towards the end of transmission of the attention preamble, as opposed to toward the beginning of transmission, so that power consumption by the implantable device is minimized.

One potential multi-step process is similar to the one step process discussed above, but the first one or more attempts to establish synchronization use an attention preamble that is shorter than the inbound listening interval. In this regard, if the transmission catches the window, the receiver of the implantable device may be held open for a shorter period of time than that resulting from the one step process and thus a power savings in the implantable device may be achieved. However, if the transmission is not received, one or more subsequent messages will need to be sent, with the associated inconvenience of an extra time delay. In this process, the first message is preferably centered around the external communication device's best estimate as to inbound listening period. If communication and synchronization are not reestablished in response to the first message, one or more subsequent messages may be transmitted with longer attention preambles that still may be shorter than the interval between inbound time slots, equal to it, or even greater than it. In any event, if communication and synchronization are not reestablished using the previous attempts, a final message will be sent with an attention preamble of length equal to or greater than the inbound listening interval. If communication hasn't been reestablished based on transmitting attention preamble for a period of time equal to or somewhat greater than the normal operation inbound listening interval, it may be appropriate to send an attention preamble for a time period equal to or somewhat greater than the storage mode inbound listening interval as the system may have inadvertently been shifted to that mode. If communication is still not established, the patient may be alerted to the problem so that he/she may reposition the external communication device relative to the implantable device, go to a different location where electromagnetic interference may be reduced, or otherwise seek assistance in addressing the problem.

As a second example of a potential multistep synchronization process the length of the attention preamble may not be increased beyond that selected for the first attempt, instead if multiple attempts are needed, the start time of transmission may be shifted such that the entire set of messages, if required to be sent, will cover all possible portions of the inbound listening interval by covering a different portion of each interval in a series of intervals.

As a final alternative, if unsolicited communications are outbound from the implantable device on a periodic basis, the external communication device may simply open its reception window for the entire interval between at least two of the successive periodic outbound communications so the message known to be transmitted sometime during the interval will be received if the devices are within telemetry range and other problems are not present thus enabling synchronization at least in part reestablished.

As messages may have different levels of criticality, a higher level of error checking may be appropriate for some messages while a lower level of error checking may be acceptable for other messages. In the present embodiment, all transmissions include some type of error checking or validation code where more critical messages are provided with a more secure code. In the present embodiment, multiple levels of security have been defined. In particular, three levels of security have been established. In other embodiments fewer or greater numbers of levels may be used. In the present embodiment, the three levels of security or criticality are known as (1) status, (2) command, and (3) critical. Status messages are the least critical and they are transmitted with a 1-byte CRC code. Periodic status updates and response messages are examples of this message type. Command messages are of intermediate criticality and are transmitted with a 16-bit CRC code. Critical messages are of the highest criticality and are subjected to the highest level of security. These messages are used to establish insulin delivery. Critical messages are transmitted with a 16-bit CRC and with duplicate data in the data portion of the message. The receiver verifies that both copies of the data are identical before using the message. Furthermore, various delivery amounts indicated in the messages may be compared to various predefined maximum amounts to confirm that they are within reasonable limits.

An example of an exception to the above preferred duplicating of transmitted data, occurs with the set basal profile message which transmits 48 basal amounts for use during each of 48 half-hour periods during a day. Due to the length of this message, duplicate data is not transmitted but the various basal rate amounts are compared to maximum basal rate amounts programmed into the system.

In alternative embodiments, duplicate data transmission may be eliminated as an unnecessary precaution. Comparison of transmitted duplicate data can be more generally implemented or eliminated as an unnecessary precaution. In still further alternative embodiments, additional or other security precautions may be implemented such as, for example, transmitting the desired data once but also transmitting a selected computed value that is derived from selected pieces of critical data that are intended to be in the message.

Some messages may be transmitted without expecting a response, in which case the sender will not know whether they were correctly received (non-response transactions). Other messages may require a response. If a response to these messages is not received, the transmitter will respond to the failure by repeating the transmission of the message. After a predefined number of transmission attempts without a response, the message may be declared undeliverable, and the patient may be alerted to the problem. In the present embodiment, outbound status messages do not require a response.

All messages (with the exception of the link message and the interrogate message) that require a response and trigger an action in the receiver, and all responses to such messages, are transmitted with a sequence number. In the present embodiment, that sequence number is a single bit that identifies the sequence of messages. As such, this sequence number is toggled between its two possible states "1" and "0", by the transmitter each time a message is sent and the appropriate response (including the sequence number) is received. The receiver toggles its concept of what the sequence number should be when it receives a valid message with the sequence number that it is next expecting. If it receives a message with a sequence number it is not expecting, it sends a response indicating that the message was received but does not act upon the content in the message. In alternative embodiments, the sequence numbering may be removed or enhanced to include more than one bit. The sequence number is used to ensure that a given message is only acted upon once, though the message may be received multiple times and multiple responses sent out. This situation may occur when the sender does not receive the response and then automatically resends the message one or more times. The sender waits for a response with the appropriate sequence number and it disregards any other responses with other sequence numbers. If a response is not received after one or more attempted retransmissions, the synchronization process is attempted. If that fails, the patient is alerted to the condition so that subsequent steps may be taken. In any event, once communication is reestablished, the message is resent and an appropriate response looked for. If the original message was not received in the original transmission attempts, and was only received in the last transmission attempt, and it dealt with an insulin delivery issue that was not longer applicable, the delivery could be canceled by going into a suspend mode or by taking other steps in a timely manner. Suspend mode is an operational state of the implantable device where insulin delivery is reduced to a medically insignificant level.

If a received message requires a response, the recipient responds during the next available transmission period. If a received message has an incorrect CRC, it is ignored. In the present embodiment, the sender of a messages waits a predetermined period of time for the anticipated response message and if it does not receive the response as expected, it takes the appropriate course of action as noted above.

In the present embodiment, software version numbers are included with software updates to allow upgradability of software functionality and to ensure compatibility between external communication devices and their software versions and implantable devices and their software versions. A 2-byte version number is assigned to all versions of the telemetry system. 1-byte is used for a telemetry version number and the other is for the telemetry revision number within that version.

Subsequent versions of the telemetry software are numbered such that when changes to the protocol create incompatibilities with earlier releases, a new version number is used and the revision number is set to zero. When a new version of the telemetry software is compatible with previous versions, the software version number is unchanged but the revision number is incremented. An application number may also be applied to the software and checked for compatibility to avoid problems associated with mismatching of external communication devices and implantable devices where the software in each may be designed for different applications, such as delivering different types of drugs, for operating with different units of measurement, or for controlling systems with different hardware.

The user may need to change the time defined in the external communication device. This may result from changes when traveling between time zones, due to annual shifts in time, as well as due to slight errors in tracking time. In the present embodiment, the external communication device keeps track of minutes, hours, and days based on the operation of its clock and any updates from a user. The external communication device receives it concept of seconds within a minute from that found in the implantable device and as such does not allow user input to update a second value. When the user changes the time on the external communication device, an appropriate message is transmitted to the implantable device so that it may adapt to the new time of day. This is done because certain automatic delivery regimes (e.g. basal rate profiles) are based on the time of day. In the present embodiment, delivery is not automatically changed between various days of the week or month and as such the implantable device has no need of tracking this information. However, if in alternative embodiments day sensitive delivery routines are implemented in an automated manner then the external communication device could be programmed to pass this information to the implantable device which may be programmed to accept and use it. If it is found desirable for the communication device to track seconds, in an alternative embodiment, the medical device could obtain its concept of seconds from the communication device.

In some embodiments, software may be downloaded from the external communication device to the implantable device. The downloading of software may include the downloading of executable software as well as the downloading of data structures that may be used by the executable software. This downloading of software may be only allowed to occur when the implantable device is in a bootloader operation mode. The bootloader operation mode is an intermediate operation state where various communication activities can occur but where medical functionality of the implantable device is inactivated or strictly limited to a default mode of simplified operation. New software may be of the application type or of the bootloader type. In the present embodiment, new application software is always loaded for both the main and monitor processors at the same type. Replacement bootloader software may be loaded for either processor individually. Application software is the software that controls normal medical operation of the device along with telemetry operations when it is in control of the device. Bootloader software is the software that initially controls of the device immediately after start up and resetting. As such, in more preferred embodiments, the software controlling the implantable device will allow certain communication operations to occur and will also allow either the downloading of new software or the normal medical operations of the device but not both simultaneously. In alternative embodiments, device operation may be modified so that application software may be loaded to either processor individually or so that downloading of software need not be limited to periods when the bootloader software is being executed.

The bootloader mode may be initiated in the implantable device by sending it a reset message from the external communication device. Downloading may be initiated by using a inbound load start message that includes an overall validation code (e.g. CRC) for the program that is to be downloaded (i.e. software image) along with its normal message validation code (e.g. CRC) that is used to confirm that the start download message itself was properly received. The software may be downloaded from a non-volatile memory module (e.g. a SEEPROM) in the external communication device, or from a second external device, that holds implantable device software. Downloads then occur using one or more inbound load continue messages each having data portions (excluding op-code and validation code). In the present embodiment, when loading application software, the inbound load start and inbound load continue messages are sent in series four times one for each of two images for the main processor (one executable and one data) and for each of two images for the monitor processor (one executable and one data). Each message that is sent carries its own validation code, that must be acknowledged as valid if the message is to be accepted and acknowledged before additional messages are sent.

Once all program images have been downloaded, the new code is executed by transmitting a bootstrap message. A final validation code (e.g. CRC) for each program image that is supplied by the external communication device is compared to a validation code (e.g. CRC) that is derived for each program image directly from the data that was received. For each calculated program image validation code that doesn't match the transferred validation code, an error message is sent to the external communication device and that program image is completely reloaded. In any event, until all programs are confirmed to have been appropriately received, the implantable device remains in bootloader mode. Once each calculated validation code and each transmitted validation code match for each program image, the CPU is commanded to turn over control of each processor IC to its respective program. If the downloaded programs are replacement bootloader programs, once the validation codes (e.g. CRCs) are confirmed, the program images are copied over into their permanent positions within a non-volatile memory module and the device is reset so that upon reboot, the new bootloader code is executed.

In alternative embodiments, after each image is downloaded, a calculated validation code (e.g. CRC) may be compared to a transmitted validation code so that the program image may be confirmed as being properly received or be reloaded until it is properly received prior to continuing with the loading of any additional software images.

In alternative embodiments, instead of an overall CRC being sent for each program, two overall CRCs may be sent where one is for the monitor processor IC images that were transmitted while the other is for the main processor IC images that were transmitted. In still other embodiments, a single overall CRC may be transmitted for all programs regardless of the processor IC on which they will be used.

The transmitted CRCs, the initially calculated CRCs (once confirmed to be correct), a CRC based on an initially configured software image (if not completely configured at the time of transfer), or other validation code may be retained by the implantable device and used to periodically confirm the continued proper configuration (i.e. that the software has not been corrupted) of the software images is retained and used by the implantable device.

In the present embodiment, a specific external communication device is configured/programmed to communicate substantively with only one specific implantable device, that is in turn configured/programmed to communicate substantively with only the same specific external communication device. An external communication device is capable of retaining the telemetry ID of exactly one implantable device at a time and an implantable device is capable of retaining the telemetry ID of exactly one external communication device at a time. A small amount of non-substantive communication (i.e. communication that does not impact insulin delivery) can occur between external communication devices and implantable devices that are not linked (i.e. partnered or married) to one another (i.e. provided with each others telemetry IDs).

When it is necessary to link an external communication device to an implantable device, the following process may be carried out used.

(1) The linking process is initiated by an external communication device sending an interrogate message. The interrogate message is sent using the universal telemetry ID with a CRC code that is not based on telemetry IDs. All implantable devices that are within telemetry range receive the message. The interrogate message transmits, among other things, an exclusion list that contains up to eight telemetry IDs of implantable devices to which the external communication device is not to be linked. The first time that the interrogate message is sent out during a given linking cycle, all eight IDs in the exclusion list are blank. All implantable devices that are within telemetry range and that are not in the exclusion list respond to the interrogate command. If there is more than one implantable device within telemetry range, multiple responses may be sent to the external communication device, however the external communication device will pick up only the first of such responses. The response will contain personal ID information from implantable device. The personal ID of the implantable device contains user identity information that was programmed into the implantable device. The personal ID of the implantable device is displayed on the external communication device display for verification by the user.

(2) The implantable device is then either accepted or rejected by the user, based on the personal ID information that is provided. The user will reject the implantable device if the personal ID information indicates that the wrong implantable device has responded. If the implantable device is rejected, the telemetry ID of the implantable device is added to the exclusion list and the interrogate message is resent. This time the previously rejected implantable device will not respond to the interrogate message. The process of rejecting implantable devices may continue a plurality of times. If after the eighth attempt, a wrong implantable device is still responding to the interrogate message, the user must relocate himself/herself to a location away from other implantable devices so that only the proper device will respond.

(3) Once the desired implantable device has responded, been received, and is accepted, a link external communication device to implantable device message is transmitted to the specific implantable device using its telemetry ID along with the telemetry ID of the external communication device.

(4) The implantable device responds to the link message, and the process is complete. The implantable device and external communication device are now linked and may communicate substantive information concerning medication delivery based on their specific telemetry IDs (assuming the implantable device is operating in the normal application mode as opposed to the bootloader mode discussed above).

In the present embodiment, many different types of messages and responses thereto can be written into the programs that control the implantable device and the external communication device according to the protocol features set forth above. These messages may be used for a number of different purposes. For example, (1) they may be system level messages that are used for testing devices, for resetting devices, or for establishing relationships between implantable devices and external communication devices, (2) they may be alarm messages that are used to convey alarm conditions or to clear alarm conditions, (3) they may be miscellaneous messages that set various parameters or perform various read operations, (4) they may be delivery messages that set delivery amounts, read delivery status, or set parameters such as concentration and pump stroke volume that may be required to appropriately control delivery of the drug, (5) they may be data log messages that set data log boundaries, read boundaries, or clear data logs, boundaries or read information from various data logs or supply information to those data logs, (5) they may be refill messages that are related to amounts of material that are added to the reservoir periodically, (7) they may be compound messages that perform more than one function, or (8) they may be error messages that request error condition status or supply error condition status. In other embodiments, messages may be classified in different ways. For illustrative purposes, examples of messages are provided herein next.

EXAMPLE 1

System Level—Sync Message

This message may be sent when time synchronization between the external communication device and the implantable device has been lost. The sync response, like all messages, is sent starting on the second boundary, so the subsecond information is implicitly transmitted as zeros. The sync message is sent by the external communication device with an attention preamble. When the external communication device attempts to transmit a message to the implantable device, and the external communication device does not receive a response, this message is used to regain a communication link with the implantable device. The duration of the attention preamble may be set as large as the listening interval during normal mode operation or it may be even increased further if it is believed that the implantable device may have switched into storage mode. The message may be sent using (1) the specific telemetry ID of the implantable device, (2) a 1-byte op-code without a sequence number, and (3) a 16-bit CRC.

Once the sync message is transmitted by the external communication device, it expects to the receive a response form the implantable device. This response is in the form of a sync response message. The sync response message is sent to the external communication device with (1) a 1-byte sync response op-code (no sequence number), (2) a 1-byte value supplying the number of the half hour (0 to 47) of the day under which the implantable device is operating, (3) a 1-byte value indicating the minute within the half hour (0 to 29), (4) a 1-byte value of the second within the minute (0 to 59), (5)a 1-byte value indicating the next sequence number expected by the implantable device, and (6) a 16-bit CRC. In other embodiments other information could passed with the message, more information, or less information could be passed with the message. For example, if the external communication device is only going to update its concept of seconds within a minute based on the receipt of this response message, then the response could be limited to inclusion of only that data. On the other hand, if the external communication device will compare the received minute and half hour values to its concept of those values and initiate a set current time message in return to update the implantable device's concept of time if necessary then transmission of this extra information may be useful. Alternatively, such information may also be useful if the external communication device will inform the patient of any discrepancy between the concept of time on the two devices so that the patient can make a decision as to whether the time on the implantable device should be updated to match that on the external communication device.

EXAMPLE 2

System Level—Reset Message

The reset message is used to force the implantable device software to enter bootloader mode (i.e. reload the bootloader software) and to thereby exit application mode (stop execution of application software). This message may be sent out to prepare the implantable device to accept new software that can be supplied with inbound load start message, in conjunction with the inbound load continue messages, and then to restart the application software with a bootstrap command. In embodiments where the reset operation and the reloading of the bootloader software doesn't damage the application software previously loaded in the medical device, it may be possible to simply restart the application software using the bootstrap command without first reloading it. This may be useful if for example, the reset operation was not done so that new application software could be loaded for both processors but instead was done so that new bootloader software could be loaded or so new application software could be loaded for only one of the processors. This message is sent using (1) the telemetry ID of the implantable device, (2) a 7-bit op-code, (3) a 1-bit sequence number, and (4) a 16-bit CRC. In the present embodiment, the implantable device does not supply any response to the reset message.

EXAMPLE 3

System Level—Initiate Self-Test and Response

This message triggers the implantable device software to perform self-test diagnostics. When the implantable device detects an error, the error will be transmitted in the regular outbound message slot using an error message. The response message indicates that the message was received and that the tests were initiated. The self test message is sent to the implantable device with (1) the implantable device's telemetry ID, (2) a 7-bit op-code, (3) a 1-bit sequence number, and (4) a 16-bit CRC.

The response message is sent from the implantable device to the external communication device with (1) the telemetry ID of the external communication device, (2) a 7-bit op-code, and (3) a 1-bit sequence number that corresponds to the sequence number of the original message.

EXAMPLE 4

System Level—Read Self-Test Progress

The Read Self-Test Progress message is used to determine the status of the previously requested self test. This message may be automatically sent out by the external communication device (under software control) on a periodic basis until a reply message is received indicating that the tests have been completed. This message is sent out with (1) the telemetry ID of the implantable device, (2) a 7-bit op-code, (3) a 1-bit sequence number, and (4) a 16-bit CRC.

The response message is sent from the implantable device to the external communication device using (1) the telemetry ID of the external communication device, (2) a 7-bit op-code, (3) a 1-bit sequence number matching the sequence number of the original message, (4) a 1-byte data element from which status information can be interpreted by the external communication device, and (5) a 16-bit CRC.

EXAMPLE 5

System Level—Interrogate Message

The interrogate message is used to obtain identification information from an implantable device. This command is used when the external communication device must learn the telemetry identification of the implantable device. The interrogate message initially uses an attention preamble equal to the normal mode inbound listening interval (e.g. 2 seconds). However, if there is no response, the external communication device retries with an attention preamble having a length equal to the storage mode inbound listening interval (e.g. 15 seconds). If the telemetry ID of an implantable device is in the exclusion list field of this message, that implantable device does not respond. This message is sent with (1) the universal telemetry ID rather than the specific telemetry ID of the implantable device, (2) a 1-byte op-code, (3) 3 bytes setting forth the telemetry ID of the external communication device, (4) 24-bytes setting forth telemetry IDs of excluded implantable devices, and (5) a 16-bit CRC.

The response to this message is sent to the external communication device with (1) its specific telemetry ID, (2) a 7-bit op-code, (3) a 1-bit sequence number corresponding to the value expected to be seen by the implantable device upon receipt of a next message that contains a sequence number, (4) a 1-byte bolus number indicative of the next bolus number that the implantable device expects to see when it receives a message that contains a bolus number, (5) 3 bytes setting forth the telemetry ID of the implantable device, (6) a 1-byte indication as to whether the implantable device is operating under control of application software or bootloader software, (7) a 1-byte number indicating the application under which the implantable device is being used, (8) a 2-byte designation of the telemetry version and revision number, (9) a 2-byte indication of the version and revision of the application software operating on the implantable device, (10) a 32-byte personal identification field for the pump patient, (11) a 4-byte bit field that indicates what alarms will be asserted (i.e. reasserted) by the implantable device, and (12) a 16-bit CRC.

EXAMPLE 6

System Level—Link Message

This message is used to associate an external communication device and an implantable device. This message is sent following the interrogate message and receipt of a response from the implantable device that is to be linked to. The link external communication device to implantable device message may be transmitted with an attention preamble equal to the normal mode inbound listening interval (e.g. 2 seconds). However, if there is no response, the external communication device retries with an attention preamble having a length equal to the storage mode inbound listening interval. This message is sent with (1) the telemetry ID of the implantable device, (2) a 7-bit op-code indicating that this is the link message, (3) a 1-bit sequence number set to equal the sequence number obtained from the response to the interrogate message, (4) 3 bytes of telemetry ID for the external communication device, and (5) a 16-bit CRC that is not based on the telemetry ID of the external communication device.

A response to the link message is sent from the implantable device back to the external communication device. The response to this message is sent with (1) the telemetry ID of the external communication device, (2) a 7-bit op-code indicating that it is the response to a link message, (3) a 1-bit sequence number corresponding to the value used in the link message, (4) a 4-byte bit field that indicates what alarms will be asserted (i.e. reasserted) by the implantable device, (5) a 1-byte value indicating the current half hour value since midnight, (6) a 1-byte value indicating the current minute within the half hour, (7) a 1-byte value indicating the current second within the minute, (8) a 4-byte value indicating of the number of minutes since the implantable device was first initialized, and (9) a 16-bit CRC.

EXAMPLE 7

System Level—Bootstrap

The bootstrap message is used to confirm that the CRCs of the downloaded software images are correct and then to cause both processors of the implantable device to transfer control from the bootloader software to the application software. If the calculated CRCs do not match the CRCs of the downloaded software, an error message is sent to indicate that there is an error, and the software remains in the bootloader mode. In some embodiments, this error may give rise to retransmission of all software images or only those that could not be validated. If the implantable device is operating under control of the application software when the bootloader message is received, the message is acknowledged with the bootstrap response message, however, there is no mode change. This message is sent with (1) the telemetry ID of the implantable device, (2) a 7-bit op-code indicating that this is the bootstrap message, (3) a 1-bit sequence number set to match the next sequence number expected to be received by the implantable device, and (4) a 16-bit CRC.

The response message is sent with (1) the telemetry ID of the external communication device, (2) a 7-bit op-code indicating that this message is the response to the bootstrap message, (3) a 1-bit sequence number matching the sequence number of the bootstrap message, and (4) an 8-bit CRC.

EXAMPLE 8

System Level—Inbound Load Start Message

The inbound load start message provides the means to initiate the load of the implantable device with application software. The implantable device must be running in the bootloader mode for this command to have an effect. If the implantable device is in the bootloader mode, then the inbound load start message causes the inbound load start message data to be parsed and stored into the memory locations specified by the load data field of the message. As the bootloader software expects to download a certain number of software images (e.g. 4 images—1 software code image for the monitor processor, 1 data image for the monitor processor, 1 software code image of the main processor, and 1 software data image for the main processor), the use of the inbound load start message is repeated after each download until each expected image has been downloaded. This message is sent with (1) the telemetry ID of the implantable device, (2) a 7-bit op-code indicating that the message is the inbound load start message, (3) a 1-bit sequence number matching the next sequence number expected by the implantable device, (4) a 1-byte field indicating whether the software image that will be sent is for the monitor processor or for the main processor, (5) a 2-byte number designating the segment value for the address where the software image is to start loading, (6) a 2-byte number designating the offset of the address where the software image is to start loading, (7) a 16-bit CRC for the entire software image that is to be downloaded potentially using multiple inbound load continue messages, (8) a 1-byte field indicating whether the image to be downloaded is data or program code, (9) a 1-byte field indicating the download image number, and (10) a 16-bit CRC for the message.

The response to the inbound load start message is sent to the external communication device with (1) its telemetry ID, (2) a 7-bit op-code indicating that the message is the response to an inbound load start message, (3) a 1-bit sequence number matching the sequence number used on the originating message, and (4) an 8-bit CRC.

EXAMPLE 9

System Level—Inbound Load Continue Message

The inbound load continue message is the means to load the implantable device with application software. The implantable device must be running in bootloader mode for this command to have an effect.

If the implantable device is in the bootloader mode, then the first inbound load continue message following an inbound load start message causes the load data portion of the message to be stored into the memory locations specified by the address bytes specified in the most recent inbound load start message. As the software is loaded, the address is updated by the implantable device such that subsequent inbound load continue messages have their data loaded in contiguous memory. As the external communication device is aware of the number of inbound load continue messages it will take to download the entire image, the sending of successive messages is repeated the required number of times after each message is confirmed to have been correctly received. The sending of the same message is repeated until a confirmation of its appropriate receipt is obtained or until the patient is informed of the problem so that further action may be taken. This message is sent with (1) the telemetry ID of the implantable device, (2) a 7-bit op-code indicating that the message is the inbound load continue message, (3) a 1-bit sequence number matching the sequence number that the external communication device believes that the implantable device is expecting next, (4) a 2-byte data count field indicating how many bytes of data are following in the message, (5) the number of bytes of the binary image of the software being download that were indicated in the data count field, and (6) a 16-bit CRC.

Once the data is loaded and the receipt of the message validated, the implantable device returns a response message. No response is returned if the validation of the message is not confirmed, in which case the implantable device simply awaits the resending of the message. The response message is sent with (1) the telemetry ID of the external communication device, (2) a 7-bit op-coded indicating that the message is the response to an inbound load continue message, (3) a sequence number matching the sequence number specified in the inbound load continue message, and (4) an 8-bit CRC for the message.

EXAMPLE 10

Alarm—Read Alarm Condition Message

This message requests the implantable device to return a response message that indicates the alarm condition states of the implantable device. This message is sent from the external communication device to the implantable device with (1) the telemetry ID of the implantable device, (2) a 7-bit op-code indicating that this is the read alarm condition message, (3) a 1-bit sequence number providing the sequence number next expected by the implantable device, and (4) a 16-bit CRC. The response provides (1) the telemetry ID of the external communication device, (2) a 7-bit op-code indicating that this message is a response to a read alarm conditions message, (3) a 1-bit sequence number that provides the sequence number used in the read alarm conditions message that gave rise to the response, (4) a 4-byte field indicating the current alarm state of the implantable device, (5) a 4-byte field indicating which alarms will be reasserted in the future, and (6) an 8-bit CRC

EXAMPLE 11

Alarm—Clear Alarm Condition Message

This message clears an alarm condition in the implantable device. If there is more than one alarm condition in the implantable device, each alarm condition may be cleared individually. This message is sent with (1) the telemetry ID of the implantable device, (2) a 7-bit op-code indicating that this is the clear alarm condition message, (3) a 1-bit sequence number that is next expected by the implantable device, (4) a 4-byte field indicating which alarm condition to clear, and (5) a 16-bit CRC. The response is sent with (1) the telemetry ID of the external communication device, (2) a 7-bit op-code indicating that the message is a response to the clear alarm condition message, (3) a 1-bit sequence number providing the sequence number used with the original message, (4) a 4-byte field indicating remaining alarm conditions that have not been cleared, and (5) an 8-bit CRC.

EXAMPLE 12

Miscellaneous—Read Current Time

This message reads the time in the implantable device. The message sends (1) the telemetry ID of the implantable device, (2) a 7-bit op-code indicating that the message is the read current time message, (3) a 1-bit sequence number providing the next sequence number expected the implantable device, and (4) a 16-bit CRC.

The response to this message is sent from the implantable device back to the external communication device. The response to this message is sent with (1) the specific telemetry ID of the external communication device and is sent with (2) a 7-bit op-code indicating that it is the response to a read current time message, (3) a 1-bit sequence number corresponding to the value used in the read current time message, (4) a 1-byte value indicating the current half hour value since midnight, (5) a 1-byte value indicating the current minute within the half hour, (6) a 1-byte value indicating the current second within the minute, (7) a 4-byte value indicating the number of minutes since the implantable device was first initialized, and (9) an 8-bit CRC.

EXAMPLE 13

Miscellaneous—Set Current Time

This message sets the time in the implantable device. More particularly in the present embodiment, this message sets the half hour number since midnight and the minute number within the half hour. This message does not update the implantable device's concept of what the current second is or its concept of how many minutes have lapsed since it was initialized. The primary result of this message is to synchronize the basal rate that the implantable device is delivering as compared to what the external communication device believes it should be delivering. In the present embodiment, the implantable device changes the time to the values specified in this message synchronous to the beginning of the next minute. This message is sent from the external communication device to the implantable device. It is sent to the implantable device with (1) its specific telemetry ID, (2) a 7-bit op-code indicating that it is the set current time message, (3) a 1-bit sequence number providing the next sequence number expected by the implantable device, (4) a 1-byte value indicating the current half hour value since midnight according to the external communication device, (5) a 1-byte value indicating the current minute within the half hour according to the external communication device, and (6) a 16-bit CRC.

The response to this message is sent from the implantable device to the external communication device. It is sent with (1) the telemetry ID of the external communication device, (2) a 7-bit op-code indicating that it is a response to a set current time message, (3) a 1-bit sequence number matching the sequence number of the set current time message, and (4) an 8-bit CRC.

EXAMPLE 14

Miscellaneous—Read Personal ID Message

This message reads the current value of the personal ID information previously set into the implantable medical device. This message is directed from the external communication device to the implantable device. The message sends (1) the telemetry ID of the implantable device, (2) a 7-bit op-code indicating that this is the read personal ID message, (3) a 1-bit sequence number providing the next sequence number expected by the implantable device, and (4) a 16-bit CRC.

The response to this message is sent from the implantable device to the external communication device. It is sent with (1) the telemetry ID of the external communication device, (2) a 7-bit op-code indicating that it is a response to a read personal ID message, (3) a 1-bit sequence number matching the sequence number of the read personal ID message, (4) a 32-byte field providing the personal ID information that was previously entered into the implantable device, and (5) an 8-bit CRC.

EXAMPLE 15

Miscellaneous—Set Personal ID Message

This message sets the personal ID parameter for the implantable device to that which was entered into an implantable device personal ID field in the external communication device. This message is directed from the external communication device to the implantable device. The message sends (1) the telemetry ID of the implantable device, (2) a 7-bit op-code indicating that this is the set personal ID message, (3) a 1-bit sequence number providing the next sequence number expected by the implantable device, (4) a 32-byte field that contains the personal ID information for the implantable device that was previously entered into the external communication device, and (5) a 16-bit CRC.

The response to this message is sent from the implantable device to the external communication device. It is sent with (1) the telemetry ID of the external communication device, (2) a 7-bit op-code indicating that it is a response to a set personal ID message, (3) a 1-bit sequence number matching the sequence number of the set personal ID message, and (4) an 8-bit CRC.

EXAMPLE 16

Miscellaneous—Memory Read Message

This message reads a portion of the memory in the implantable device that is requested by the user using the external communication device. This message is directed from the external communication device to the implantable device. The message sends (1) the telemetry ID of the implantable device, (2) a 7-bit op-code indicating that this is the read memory message, (3) a 1-bit sequence number providing the next sequence number expected by the implantable device, (4) a 2-byte count value indicating the number of bytes of memory to read, (5) a 2-byte value indicating the offset of the memory address where reading is supposed to initiate, (6) a 2-byte value indicating the segment of the memory address where reading is supposed to initiate, (7) a 1-byte indication as to whether the memory address is for the monitor or the main processor, and (8) a 16-bit CRC.

The response to this message is sent from the implantable device to the external communication device. It is sent with (1) the telemetry ID of the external communication device, (2) a 7-bit op-code indicating that it is a response to a read memory message, (3) a 1-bit sequence number matching the sequence number of the read memory message, (4) a 2-byte count field indicating the number of bytes of the memory image that is being supplied plus the number of bytes in the CRC, (5) a memory image having the number of bytes indicated in the count field less two, and (6) a 16-bit CRC.

EXAMPLE 17

Insulin Delivery—Set Profile Rates

This message is used to set a basal rate profile amount to be supplied during each half hour of the day. As such this message is used to set 48 different rates to be used in the delivery of basal rates of insulin. The 48 different rates are entered by the user into the external communication device either implicitly or explicitly. The external communication device calculates basal rates in units of pump strokes per minute. The stroke volume and insulin concentration are taken into account to ensure that a reasonable error tolerance is not exceeded. The implantable device compares each of the entries of the profile table field to the maximum basal rate set by a set maximums message. If any entry in the profile table is greater than the maximum basal rate, the implantable device sends an error message to the external communication device. In an alternative embodiment, the message could be ignored by the implantable device, thus forcing the external communication device to resend the message in order to receive its expected response.

The message sends the (1) telemetry ID of the implantable device, (2) a 7-bit op-code indicating that this is the set profile rates message, (3) a 1-bit sequence number providing the next sequence number expected by the implantable device, (4) a 96-byte profile table providing a 2-byte value for each rate being supplied, and (5) a 16-bit CRC.

The response to this message is sent from the implantable device to the external communication device. It is sent with (1) the telemetry ID of the external communication device, (2) a 7-bit op-code indicating that it is a response to a set profile rate message, (3) a 1-bit sequence number matching the sequence number of the set profile rate message, and (4) an 8-bit CRC.

EXAMPLE 18

Insulin Delivery—Read Profile Rates

This message causes the implantable device to return the 48 half hour basal rates (i.e. basal rate profile) currently controlling basal rate delivery in the implantable device.

The message sends (1) the telemetry ID of the implantable device, (2) a 7-bit op-code indicating that this is the read basal rate profile message, (3) a 1-bit sequence number providing the next sequence number expected by the implantable device, and (4) a 16-bit CRC.

The response to this message is sent from the implantable device to the external communication device. It is sent with (1) the telemetry ID of the external communication device, (2) a 7-bit op-code indicating that it is a response to a read basal rate profile message, (3) a 1-bit sequence number matching the sequence number of the read basal rate profile message, (4) a 96-byte field providing the basal rates for each half hour of the day, (5) a 1-byte pointer (0–47) that indicates which of the 48 basal rate values is in use by the implantable device, and (6) a 16-bit CRC.

EXAMPLE 19

Insulin Delivery—Read Lifetime Total Delivered

This message causes the implantable device to return the total number of pump strokes that have occurred since the implantable device was initialized during manufacturing. The message sends (1) the telemetry ID of the implantable device, (2) a 7-bit op-code indicating that this is the read lifetime total message, (3) a 1-bit sequence number providing the next sequence number expected by the implantable device, and (4) a 16-bit CRC.

The response to this message is sent from the implantable device to the external communication device. It is sent with (1) the telemetry ID of the external communication device, (2) a 7-bit op-code indicating that it is a response to a read lifetime total delivered message, (3) a 1-bit sequence number matching the sequence number of the read life time total delivered message, (4) a 3-byte field providing the total number of pump strokes delivered during the life of the implantable device, and (5) an 8-bit CRC.

EXAMPLE 20

Insulin Delivery—Set Temp Basal Rate

A temporary basal rate is enabled by this message. A temporary basal rate may be used to replace the basal rate that would otherwise be delivery as dictated by the current half hour and the basal rate profile discussed above. The temporary basal rate is set as a delivery rate for use during a specified time interval. A remaining duration of a temporary basal rate may be ascertained by using the read delivery status message as will be discussed hereafter. An ongoing temporary basal rate can be canceled by using the set temp basal rate message and setting the duration to zero.

After receipt, of the message and confirmation of the CRC, the implantable device verifies that several duplicate fields match: (1) the op-code field, indicating that this is the set temporary basal rate message matches the duplicate op-code field, (2) the sequence number field matches the sequence number duplicate field, (3) the temporary basal rate amount field matches the temporary basal rate amount duplicate field, and (4) the temporary basal rate duration field matches the temporary basal rate duration duplicate field. If there is a duplicated field that does not match its original, the receiver responds with an error message. The message sends (1) the telemetry ID of the implantable device, (2) a 7-bit op-code indicating that this is the set temporary basal rate message, (3) a 1-bit sequence number providing the next sequence number expected by the implantable device, (4) a 2-byte value indicating the temporary basal rate amount, (5) a 2-byte value that indicates the number of minutes that the temporary basal rate is to run, (6) a duplicate of element 2, (7) a duplicate of element 3, (8) a duplicate of element 4, (9) a duplicate of element 5, and (10) a 16-bit CRC.

The response to this message is sent from the implantable device to the external communication device. It is sent with (1) the telemetry ID of the external communication device, (2) a 7-bit op-code indicating that it is a response to a set temporary basal rate message, (3) a 1-bit sequence number matching the sequence number of the set temporary basal rate message, and (4) an 8-bit CRC.

EXAMPLE 21

Insulin Delivery—Deliver Bolus Message

This message causes the implantable device to deliver a bolus. A bolus is an amount of insulin that is dispensed in addition to the insulin rate that is being dispensed according to the basal rate profile or temporary basal rate. In a preferred implementation, the implantable device returns an error message when a bolus message is sent and there is an immediate bolus in progress, a priming bolus in progress, a diagnostic rate in progress, the implantable device is in a minimum delivery mode (i.e. suspend mode), or the implantable device is in a non-delivery mode (i.e. stop mode). According to a preferred implementation two bolus types may be provided simultaneously: (1) an immediate bolus (i.e. phase 1 bolus) amount that is to be dispensed as quickly as possible, and (2) an extended bolus (i.e. phase 2 bolus) amount that is to be dispensed as a rate over a predefined period of time. Before implementing the requested bolus, the implantable device also verifies that various duplicate fields within the message match: (1) the op-code field, indicating that the message is the deliver bolus message is the same as the duplicate op-code field, (2) the sequence number field is the same as the sequence number duplicate field, (3) the bolus number field is the same as the bolus number duplicate field, (4) the immediate bolus amount field is the same as the immediate bolus amount duplicate field, (5) the phase 2 bolus rate field is the same as the phase 2 bolus rate duplicate field, and (6) the phase 2 bolus duration field is the same as the phase 2 bolus duration duplicate field. If there is a duplicated field that does not match its original, the implantable device sends an error message to the external communication device.

The message sends (1) the telemetry ID of the implantable device, (2) a 7-bit op-code indicating that this is the deliver bolus message, (3) a 1-bit sequence number providing the next sequence number expected by the implantable device, (4) a 1-byte field supplying a bolus number, (5) a 1-byte value indicating a phase 1 bolus amount, (6) a 2-byte value indicating a phase 2 bolus rate (this may have been entered into external communication device as an amount that was converted to a rate prior to compiling the message), (7) a 1-byte value indicating the number of minutes over which the phase 2 bolus should be delivered, (8) a duplicate of element 2, (9) a duplicate of element 3, (10) a duplicate of element 4, (11) a duplicate of element 5, (12) a duplicate of element 6, (13) a duplicate of element 7, and (14) a 16-bit CRC.

The response to this message is sent from the implantable device to the external communication device. It is sent with (1) the telemetry ID of the external communication device, (2) a 7-bit op-code indicating that it is a response to a deliver bolus response message, (3) a 1-bit sequence number matching the sequence number of the deliver bolus message, (4) a 2-byte number indicating how many pump strokes were delivered in the previous phase 1 bolus, (5) a 2-byte number indicating how many pump strokes were delivered in the previous phase 2 bolus, (6) a 1-byte number indicating the duration of the previous phase 2 bolus, and (7) an 8-bit CRC.

EXAMPLE 22

Insulin Delivery—Set Insulin Concentration

This message sets the insulin concentration for the implantable device. The delivery of insulin is not influenced by the existence of this parameter in the implantable device as the external communication device determines the correct amounts to deliver based on the value of the insulin concentration stored therein and passes the delivery amounts to the implantable device in the form of the number of pump strokes. As such, the primary usefulness of this number existing in the implantable device is for permanent storage and retrieval in case the external communication device is lost or otherwise replaced. Prior to accepting the value transferred with this message the implantable device verifies that the various duplicate fields match: (1) the op-code field, indicating this is the set insulin concentration message is the same as the set insulin concentration duplicate field, (2) the sequence number field is the same as the sequence number duplicate field, and (3) the insulin concentration field is the same as the insulin concentration duplicate field. If there is a duplicated field that does not match its original, the implantable device sends an error message to the external communication device.

The message sends (1) the telemetry ID of the implantable device, (2) a 7-bit op-code indicating that this is the set insulin concentration message, (3) a 1-bit sequence number providing the next sequence number expected by the implantable device, (4) a 1-byte field that indicates the insulin concentration, (5) a duplicate of element 2, (6) a duplicate of element 3, (7) a duplicate of element 4, and (8) a 16-bit CRC.

The response to this message is sent from the implantable device to the external communication device. It is sent with (1) the telemetry ID of the external communication device, (2) a 7-bit op-code indicating that it is a response to a set insulin concentration message, (3) a 1-bit sequence number matching the sequence number of the set insulin concentration message, and (4) an 8-bit CRC.

EXAMPLE 23

Insulin Delivery—Read Insulin Concentration

This message causes the implantable device to return the insulin concentration to the external communication device. Before acting on the response to this message the external communication device verifies that various duplicate fields within the response message match: (1) the op-code field, indicating that the message is a response to a read insulin concentration message, matches the duplicate op-code field, (2) the sequence number field is the same as the sequence number duplicate field, and (3) the insulin concentration field is the same as the insulin concentration duplicate field. If there is a duplicated field that does not match its original, the external communication device sends another read insulin concentration message.

This message is sent from the external communication device to the implantable device. It is sent with (1) the telemetry ID of the implantable device, (2) a 7-bit op-code indicating that it is the read insulin concentration message, (3) a 1-bit sequence number matching next sequence number expected by the implantable device, and (4) a 16-bit CRC.

A response to the message is sent from the implantable device to the external communication device. The response message includes (1) the telemetry ID of the external communication device, (2) a 7-bit op-code indicating that it is the response to the read insulin concentration message, (3) a 1-bit sequence number matching the sequence number of the read insulin concentration message, (4) a 1-byte field providing the concentration of the insulin, (5) a duplicate of element 2, (6) a duplicate of element 3, (7) a duplicate of element 4, and (8) a 16-bit CRC.

EXAMPLE 24

Insulin Delivery—Read Maximums

This message causes the implantable device to return various maximum values associated with insulin delivery variables that are stored in the implantable device. Amounts received in telemetry messages by the implantable device may be compared to these maximums as an added safety measure for ensuring that received messages were not corrupted or the external communication device didn't act improperly. Before considering the response message to contain valid information, the external communication device verifies that several duplicate fields in the response message match: (1) the op-code field, indicating that the response message is for a read maximums message, matches the duplicate op-code field, (2) the sequence number field matches the sequence number duplicate field, (3) the maximum basal rate field matches the maximum basal rate duplicate field, (4) the maximum bolus amount field matches the maximum bolus amount duplicate field, and (5) the maximum lock state field matches the maximum lock states duplicate field. If a duplicated field does not match its original, the external communication device resends a read maximum message to the implantable device.

This message is sent from the external communication device to the implantable device. It is sent with (1) the telemetry ID of the implantable device, (2) a 7-bit op-code indicating that it is the maximums message, (3) a 1-bit sequence number matching next sequence number expected by the implantable device, and (4) a 16-bit CRC.

A response to the message is sent from the implantable device to the external communication device. The response message includes (1) the telemetry ID of the external communication device, (2) a 7-bit op-code indicating that it is the response to the read maximums message, (3) a 1-bit sequence number matching the sequence number of the read maximums message, (4) a 2-byte value indicating a maximum acceptable value for any basal rate excluding a diagnostic rate, (5) a 1-byte value indicating a maximum number of pump strokes that can be delivered in a phase 1 bolus, (6) a 1-byte value indicating whether maximums can be changed by the patient or whether a supervisor or physician password is required to change them, (7) a duplicate of element 2, (8) a duplicate of element 3, (9) a duplicate of element 4, (10) a duplicate of element 5, (11) a duplicate of element 6 and (8) a 16-bit CRC.

EXAMPLE 25

Insulin Delivery—Set Maximums

The user interface for this message sets the delivery maximums while the message itself transfers them to the implantable device. As with most other delivery related messages various message fields are duplicated to enhance confidence that the received message has not been corrupted. The implantable device verifies that duplicate fields in the message match one another: (1) the op-code field, that indicates the message is the set maximums message, matches the op-code duplicate field, (2) the sequence number field matches the sequence number duplicate field, (3) the maximum basal rate field matches the maximum basal rate duplicate field, (4) the maximum bolus amount field matches the maximum bolus amount duplicate field, and (5) the maximum lock state field matches the maximum lock states duplicate field. If there is a duplicated field that does not match its original, the implantable device reports and error back to the external communication device.

The message sends (1) the telemetry ID of the implantable device, (2) a 7-bit op-code indicating that this is the set maximums message, (3) a 1-bit sequence number providing the next sequence number expected by the implantable device, (4) a 2-byte value that sets a maximum acceptable value for any basal rate excluding a diagnostic rate, (5) a 1-byte value that sets a maximum number of pump strokes that can be delivered in a phase 1 bolus, (6) a 1-byte value indicating whether maximums can be changed by the patient or whether a supervisor or physician password is required to change them, (7) a duplicate of element 2, (8) a duplicate of element 3, (9) a duplicate of element 4, (10) a duplicate of element 5, (11) a duplicate of element 6, and (12) a 16-bit CRC.

The response to this message is sent from the implantable device to the external communication device. It is sent with (1) the telemetry ID of the external communication device, (2) a 7-bit op-code indicating that it is a response to a set maximums message, (3) a 1-bit sequence number matching the sequence number of the set maximums message, and (4) an 8-bit CRC.

EXAMPLE 26

Insulin Delivery—Read Delivery Status

This message returns various values related to insulin delivery. The message sends (1) the telemetry ID of the implantable device, (2) a 7-bit op-code indicating that this is the read delivery status message, (3) a 1-bit sequence number providing the next sequence number expected by the implantable device, and (4) a 16-bit CRC. Unlike most other insulin delivery related messages this message does not include duplicate fields.

The response to this message is sent from the implantable device to the external communication device. It is sent with (1) the telemetry ID of the external communication device, (2) a 7-bit op-code indicating that it is a response to a read delivery status message, (3) a 1-bit sequence number matching the sequence number of the read delivery status message, (4) a 2-byte value indicating the current basal rate value that is being delivered, (5) a 1-byte profile index indicating the profile basal rate that is running (unless the profile is overridden by a diagnostic rate or a temporary rate.), (6) a 2-byte value indicating any remaining amount from an immediate bolus that is yet to be delivered, (7) a 1-byte value that indicates the number of minutes remaining until completion of delivery of a phase 2 bolus, (8) a 2-byte value indicating the delivery rate of any phase 2 bolus that is in progress, (9) a 1-byte value indicating what the present delivery mode is (i.e. normal, suspend mode, stop mode, diagnostic rate delivery mode, priming bolus mode, or storage mode), (10) remaining temporary basal rate duration, and (11) an 8-bit CRC.

EXAMPLE 27

Insulin Delivery—Set Delivery Mode

This message is used to change the delivery mode of the implantable device and to set certain delivery parameters. For added safety, the implantable device may limit what mode transitions are possible. The implantable device and/or external communication device may be programmed to require a confirmation entry be made or message be sent prior to actually making some mode transitions.

The implantable device verifies that several duplicate fields within the message match prior to accepting the validity of the message conveyed: (1) the op-code field, indicating that the message is the set delivery mode message, is the same as the duplicate op-code field, (2) the sequence number field is the same as the sequence number duplicate field, (3) the delivery mode field is the same as the delivery mode duplicate field, (4) the priming bolus amount field is the same as the priming bolus amount duplicate field, and (5) the diagnostic rate field is the same as the diagnostic rate duplicate field. If there is a duplicated field that does not match its original, the implantable device sends an error message to the external communication device.

The message sends (1) the telemetry ID of the implantable device, (2) a 7-bit op-code indicating that this is the set delivery mode message, (3) a 1-bit sequence number providing the next sequence number expected by the implantable device, (4) a 1-byte field that sets the delivery mode to one of the normal mode, suspend mode, stop mode, diagnostic rate mode, priming bolus mode, or storage mode, (5) a 2-byte value that sets the number of pump strokes to be used when delivering a priming bolus, (6) a 2-byte value setting the diagnostic basal rate in terms of a number of pump strokes per minute, (7) a duplicate of element 2, (8) a duplicate of element 3, (9) a duplicate of element 4, (10) a duplicate of element 5, (11) a duplicate of element 6, and (12) a 16-bit CRC.

The response to this message is sent from the implantable device to the external communication. It is sent with (1) the telemetry ID of the external communication device, (2) a 7-bit op-code indicating that it is a response to a set delivery mode message, (3) a 1-bit sequence number matching the sequence number of the set delivery mode message, and (4) an 8-bit CRC.

EXAMPLE 28

Refill—Set Refill Counter and Alarm Thresholds

This message is used to set various refill parameters. The message sends (1) the telemetry ID of the implantable device, (2) a 7-bit op-code indicating that this is the set refill counter and alarm threshold message, (3) a 1-bit sequence number providing the next sequence number expected by the implantable device, (4) a 2-byte value that defines the number of pump strokes of medication that was added to the reservoir after emptying it during the refill process, (5) a 2-byte value that defines the number of pump strokes of medication that remain in the reservoir when the low reservoir alarm is first triggered, (6) a 2-byte value that defines the number of pump strokes of medication that remain in the reservoir when the empty reservoir alarm is first triggered, and (7) a 16-bit CRC.

The response to this message is sent from the implantable device to the external communication. It is sent with (1) the telemetry ID of the external communication device, (2) a 7-bit op-code indicating that it is a response to a set refill counter and alarm threshold message, (3) a 1-bit sequence number matching the sequence number of the set refill counter and alarm threshold message, and (4) an 8-bit CRC.

EXAMPLE 29

Refill—Read Refill Counter and Alarm Thresholds

This message causes the implantable device to return current values of various refill parameters. This message is sent from the external communication device to the implantable device. It is sent with (1) the telemetry ID of the implantable device, (2) a 7-bit op-code indicating that it is read refill counter and alarm threshold message, (3) a 1-bit sequence number matching the next sequence number expected by the implantable device, and (4) a 16-bit CRC.

The response to this message sends (1) the telemetry ID of the external communication device, (2) a 7-bit op-code indicating that this is a response to the read refill counter and alarm threshold message, (3) a 1-bit sequence number providing the same sequence number as used with the originating message, (4) a 2-byte value that defines the number of pump strokes of medication that was added to the reservoir during the last refill process, (5) a 2-byte value that defines the number of pump strokes of medication that remain in the reservoir when the low reservoir alarm is first triggered, (6) a 2-byte value that defines the number of pump strokes of medication that remain in the reservoir when the empty reservoir alarm is first triggered, (7) a 2-byte value that indicates the remaining number of pump strokes of medication in the reservoir, and (8) a 16-bit CRC.

As illustrated by the above examples, the telemetry protocol elements of the present embodiment can be used to provide many different types of messages that can be used in transferring software, commands, and information that is useful to the robust, effective, reliable, and safe operation of an implantable medical device and more generically for an ambulatory medical device. It will be understood by those of skill in the art that many other messages types may be defined and transferred. For example messages may be defined and transferred that relate to how data logs are defined and read, how errors are communicated, and the like.

While the above embodiment has primarily been concerned with an implantable infusion pump that dispenses insulin using a piston type pump mechanism, the telemetry protocol elements may be used in other ambulatory devices such as implantable pacemakers, defibrillators, other implantable tissue stimulators, implantable physiologic sensors such as electrochemical oxygen sensors, peroxide sensors, or enzymatic sensors such as glucose sensors, externally carried infusion pumps, implantable infusion pumps that use other pumping mechanisms or simply used excess pressure and controlled flow elements to infuse various medications and drugs such as analgesics, drugs for treating AIDS, drugs for treating psychological disorders and the like. For example, the telemetry protocol of the instant embodiment may be used with an external infusion pump that may or may not have a built in display and keypad but is equipped with a telemetry system that can communicate with a physically separated communication device so that the pump need not be accessed in order to provide commands to it and receive data from it.

In these various alternatives, the physical, electronic, and programmed features of the communication device and implantable device may have different components and features than presented above for the implantable pump system so that their desired medical functionality and safety requirements are achieved and such that appropriate control and feedback is provided between the medical device and its communication device.

In other alternative embodiments the medical device may include two medical devices such as an implantable pump and an implantable sensor. The pump may dispense a drug whose physiological impact on the body (e.g. analgesic impact) is ascertained by the sensor or alternatively the sensor may supply a physiological reading that indicates a need for infusion of the drug. The pump may operate in a closed loop manner with the sensor or it may operate in an open loop manner where the patient is required to interpret sensor output information and is required to issue appropriate infusion commands to the pump. For example, in the case of a diabetic patient, the drug may be insulin and the sensor may detect glucose level.

In embodiments that include two implanted medical devices the two medical devices may be implanted adjacent one another or at an extended distance from one another. If not placed in physical contact with one another, a lead may be used to provide power conduction from one device to the other and also be used to conduct communication signals between the devices. Alternatively, each device may include at least one telemetry system that allows direct communication between them or allows indirect communication to occur via the external communication device or other external device. Each device may be supplied with its own power supply. Depending on the communication requirements each device may use two way communication (i.e. both outbound and inbound communication) or allow only one way communication (i.e. outbound communication or possibly inbound communication). Various telemetry systems may be used. For example, telemetry systems may be of the analog type, digital type, or mixed. They may be RF based, IR based, optically based, inductively based, acoustically based, have some other basis that allows communication signals to be transmitted safely through the body and picked up by the receiver.

In other alternatives, both the medical device and the communication device may be external devices (e.g. an external pump and an external RF telemetry based communication device). In still further alternatives, a first type of medical device may be implanted (e.g. an infusion pump or a sensor) while a second medical device may be external (e.g. the opposite of a sensor or an infusion pump). Where at least one of the medical devices is external, it may also function as the communication device for the other medical device in which case it may possess a display for providing information to the patient and a keypad for allowing entry of commands for issuance to the implantable device as well as for direct use by itself. Even if at least one of the medical devices is external, it may be inconvenient to access that device when information is needed or commands must be given, as such an external, non-medical communication device may be supplied that has information output (e.g. display) capabilities and input (e.g. keypad) capabilities. If a separate communication device is provided, the external medical device may or may not have display and input capabilities.

The telemetry protocol elements of the present embodiment may be used with other forms of distant communication (e.g. between the implantable device and other external devices or between the external communication device and other external devices) via various electromagnetic links like IR, optical links, longer or shorter wavelength RF, audio links, ultrasonic links, and the like.

Various elements of the telemetry protocol may be used in combination or separately to enhance communications between ambulatory medical devices and communication devices and/or controllers associated therewith.

In other embodiments two independent processors may be used that operate from a single timing chain. In these alternatives, it is preferable that at least one of the timing signals (e.g. one of the lower frequency timers) be monitored by an independently timed watchdog circuit to reduce the risk of timing problems going undetected.

In still additional embodiments, an implantable glucose sensor may be used in conjunction with an implantable insulin pump to provide feedback to the patient or physician on the effectiveness of the insulin delivery system. The patient could use the feedback to assist in making insulin delivery decisions in an open loop manner. Alternatively, the operation of the pump could be tied to the sensor output in a more or less closed loop manner to give a more automated character to system operation. Insulin may be infused without any user intervention, without pre-delivery information, and even without direct post delivery feedback. In a less automated closed loop system, drug infusion recommendations could be derived by the system and presented to the user before delivery or the system could require user acknowledgment prior to proceeding with delivery for amounts or rates exceed a predefined limit. The implantable sensor may have its own power supply or may receive power from the control circuitry provided within the pump housing through a physical lead that connects them. Power may be supplied through one or more independent leads or alternatively may be transferred over one or more data lines through the communication signals themselves. Communication may be exchanged in various ways including, for example, via galvanic leads, RF telemetry, fiber optics, and the like, and may be of digital, analog, or combined form. The sensor system may include a plurality of sensor elements which might allow continued glucose data to be supplied even though some portion of the sensors stop operating, lose calibration or produce questionable readings. The most preferred sensors would include electronic processing capability in the form of an integrated circuit mounted in or forming a part of a housing for the sensor. This configuration has the advantage of allowing digital communications between the physical sensor and any separated electronic control module.

Further teachings concerning implantable sensors and implantable sensor systems are found in a number of patents issued to D. A. Gough, including (1) U.S. Pat. No. 4,484,987, entitled "Method And Membrane Applicable To Implantable Sensor"; (2) U.S. Pat. No. 4,627,906, entitled "Electrochemical Sensor Having Improved Stability"; (3) U.S. Pat. No. 4,671,288, entitled "Electrochemical Cell Sensor For Continuous Short-Term Use In Tissues And Blood"; (4) U.S. Pat. No. 4,703,756, entitled "Complete Glucose Monitoring System With An Implantable Telemetered Sensor Module"; and (5) U.S. Pat. No. 4,781,798, entitled "Transparent Multi-Oxygen Sensor Array And Method Of Using Same". Each of these patents is incorporated herein by reference as if set forth in full.

Still further teachings concerning implantable sensors and sensor systems are found in a number of patents issued to J. H. Schulman, et al., including (1) U.S. Pat. No. 5,497,772, entitled "Glucose Monitoring System"; (2) U.S. Pat. No. 5,651,767, entitled "Replaceable Catheter System for Physiological Sensors, Stimulating Electrodes and/or Implantable Fluid Delivery Systems"; (3) U.S. Pat. No. 5,750,926, entitled "Hermetically Sealed Electrical Feedthrough For Use With Implantable Electronic Devices"; (4) U.S. Pat. No. 6,043,437, entitled "Alumina Insulation for Coating Implantable Components and Other Microminiature Devices"; (5) U.S. Pat. No. 6,088,608, entitled "Implantable Sensor and Integrity Test Therefor"; and (6) U.S. Pat. No. 6,119,028, entitled "Implantable Enzyme-Based Monitoring Systems Having Improved Longevity Due to Improved Exterior Surfaces". Each of these patents is incorporated herein by reference as if set forth in full.

Additional further teachings concerning implantable sensors and sensor systems are found in (1) U.S. Pat. No. 5,917,346, issued to J. C. Gord, et al., and entitled "Low power current-to-frequency converter"; (2) U.S. Pat. No. 5,999,848, issued to J. C. Gord, and entitled "Daisy Chainable Sensors for Implantation in Living Tissue"; (3) U.S. Pat. 5,999,849, issued to L. D. Canfield, et al., and entitled "Low Power Rectifier Circuit for Implantable Medical Devices"; and (4) U.S. Pat. No. 6,081,736, issued to M. S. Colvin, et al., and entitled "Implantable Enzyme-Based Monitoring Systems Adapted for Long Term Use". Each of these patents is incorporated herein by reference as if set forth in full.

Further teachings concerning implantable infusion pumps are found in a number of patents by R. E. Fischell, including (1) U.S. Pat. No. 4,373,527, entitled "Implantable, Programmable Medication Infusion System"; (2) U.S. Pat. No. 4,494,950, entitled "Infusion Device Intended for Implantation in a Living Body"; (3) U.S. Pat. No. 4,525,165, entitled "Fluid Handling System for Medication Infusion System", (4) U.S. Pat. No. 4,573,994, entitled "Refillable Medication Infusion Apparatus"; (5) U.S. Pat. No. 4,594,058, entitled "Single Valve Diaphragm Pump with Decreased Sensitivity to Ambient Conditions"; (6) U.S. Pat. No. 4,619,653, entitled "Apparatus For Detecting At Least One Predetermined Condition And Providing An Informational Signal In Response Thereto In A Medication Infusion System"; (7) U.S. Pat. No. 4,661,097, entitled "Method for Clearing a Gas Bubble From a Positive Displacement Pump Contained Within a Fluid Dispensing System"; (8) U.S. Pat. No. 4,731,051, entitled "Programmable Control Means for Providing Safe and Controlled Medication Infusion"; and (9) U.S. Pat. No. 4,784,645, entitled, "Apparatus For Detecting A Condition Of A Medication Infusion System And Providing

*An Informational Signal In Response Thereto"*. Each of these patents is incorporated herein by reference as if set forth in full.

Still further teachings concerning infusion pumps are found in a number of patents by Franetzki, including (1) U.S. Pat. No. 4,191,181, entitled "Apparatus For Infusion of Liquids", (2) U.S. Pat. No. 4,217,894, entitled "Apparatus for Supplying Medication to the Human or Animal Body"; (3) U.S. Pat. No. 4,270,532, entitled "Device for the Pre-programmable Infusion of Liquids"; (4) U.S. Pat. No. 4,282,872, entitled "Device for the Pre-programmable Infusion of Liquids", U.S. Pat. No. 4,373,527, entitled "Implantable, Programmable Medication Infusion System"; (5) U.S. Pat. No. 4,511,355, entitled "Plural Module Medication Delivery System", (6) U.S. Pat. No. 4,559,037, entitled "Device for the Pre-programmable Infusion of Liquids"; (7) U.S. Pat. No. 4,776,842, entitled "Device for the Administration of Medications". Each of these patents is incorporated herein by reference as if set forth in full.

Teachings concerning tissue stimulators are found in a number of patents by J. H. Schulman, including (1) U.S. Pat. No. 5,193,539, entitled *"Implantable microstimulator"*; (2) U.S. Pat. No. 5,193,540; entitled *"Structure and Method of Manufacture of an Implantable Microstimulator"*; and (3) U.S. Pat. No. 5,358,514, entitled *"Implantable Microdevices with Self Attaching Electrodes"*. Further teachings are also found in (1) U.S. Pat. No. 5,957,958, by Loeb et al., entitled *"Implantable nerve or muscle stimulator e.g. a cochlear prosthesis"*, in (2) U.S. Pat. No. 5,571,148, by G. E. Loeb, et al., entitled *"Implantable Multichannel Stimulator"*; and in (3) PCT Publication No. WO 00/74751, by A. E. Mann, and entitled *"Method and Apparatus for Infusing Liquids Using a Chemical Reaction in an Implanted Infusion Device"*. Each of these publications is incorporated herein by reference as if set forth in full.

The control of an implantable sensor could be provided through the functionality of one or both Processor ICs. One Processor IC could supply power and/or control signals to the sensor(s) and receive data back from the sensor, while the other processor could monitor the activity to ensure that sensor activity meets certain predefined guidelines.

In other embodiments, the External Communication Device of the first embodiment could be functionally linked to an external glucose sensor system such as the continuous glucose monitoring system (CGMS) offered by Minimed Inc. of Northridge, Calif. The link may be established, for example, through a physical lead or by RF telemetry.

In other embodiments other implantable, or external, sensor systems that measure something other than glucose could also be functionally coupled to the implantable device either to receive power and/or to provide data. Other such sensors might include oxygen sensors, peroxide sensors, pulse rate sensors, temperature sensors, accelerometers, and the like.

In still other alternative embodiments, the electronic control system of the first embodiment could be configured to control one or more implantable sensors or electrical stimulators with or without infusion functionality incorporated into the implantable device.

Further embodiments will be apparent to those of skill in the art upon review of the disclosure provided herein. Still further embodiments may be derived from the teachings set forth explicitly herein in combination with the teachings found in the various patent applications.

While the description herein sets forth particular embodiments, it is believed that those of skill in the art will recognize many variations to the presented embodiments based on the teachings herein, as such it is believed that many additional modifications may be made without departing from the spirit of the teachings herein. The accompanying claims are intended to cover such modifications as would fall within the true scope and spirit of the present invention.

The disclosed embodiments are therefore to be considered as illustrative and not necessarily restrictive, the scope of the invention being indicated by the appended claims, rather than the foregoing description, and all changes which come within the meaning and range of equivalency of the claims are therefore intended to be embraced therein.

We claim:

1. A medical system, comprising:
    a) an ambulatory medical device (MD) comprising MD electronic control circuitry that further comprises at least one MD telemetry system and at least one MD processor that controls, at least in part, operation of the MD telemetry system and operation of the medical device, wherein the medical device is configured to provide a treatment to a body of a patient or to monitor a selected state of the body, and
    b) a communication device (CD) comprising CD electronic control circuitry that further comprises at least one CD telemetry system and at least one CD processor that controls, at least in part, operation of the CD telemetry system and operation of the communication device, wherein the CD telemetry system sends messages to or receives messages from the MD telemetry system,
    wherein the MD telemetry system is configured to perform a bit pattern recognition that allows a selected level of fault tolerance in concluding that a selected portion of a message matches an expected pattern to be received.

2. The system of claim 1 wherein a first portion of the MD telemetry system is incorporated into the MD processor and a second portion of the MD telemetry system is external to the MD processor, or wherein a first portion of the CD telemetry system is incorporated into the CD processor and a second portion of the CD telemetry system is external to the CD processor.

3. The system of claim 2 wherein (1) the MD electronic control circuitry comprises at least one external MD functional module, other than the second portion of the MD telemetry system, that is external to the MD processor, (2) the CD electronic control circuitry comprises at least one external CD functional module, other than the second portion of the CD telemetry system, that is external to the CD processor, (3) the MD processor comprises an internal MD CPU and at least one other internal MD functional module, or (4) the CD processor comprises an internal CD CPU and at least one other internal CD functional module.

4. The system of claim 1 wherein the bit pattern recognition and the fault tolerance analysis is performed by hardware components.

5. The system of claim 1 wherein at least part of the bit recognition or fault tolerance analysis is performed via software that is being executed by a microprocessor that is operating within the medical device.

6. The system of claim 1 wherein the selected portion of the message is a preamble that is intended to hold the attention of the MD telemetry system for a period of time.

7. The system of claim 6 wherein the period of time is controlled by the length of time that the preamble is being received by the MD telemetry system.

8. The system of claim 6 wherein the period of time is about 24-bit times or more.

9. The system of claim 8 wherein the period of time is about 48-bit times or more.

10. The system of claim 8 wherein the period of time is about 96-bit times or more.

11. The system of claim 1 wherein the fault tolerance is greater than or equal to 1-bit out of 256-bits.

12. The system of claim 11 wherein the fault tolerance is greater than or equal to 1-bit out of 128-bits.

13. The system of claim 12 wherein the fault tolerance is greater than or equal to 1-bit out of 64-bits.

14. The system of claim 1 wherein the fault tolerance is less than or equal to 32-bits out of 256-bits.

15. The system of claim 1 wherein the fault tolerance is less than or equal to 8-bits out of 128-bits.

16. The system of claim 1 wherein the fault tolerance is less than or equal to 4-bits out of 64-bits.

17. The system of claim 1 wherein the fault tolerance is between 1 out of 64-bits and 4 out of 64-bits, inclusive.

18. The system of claim 1 wherein the medical device comprises an implantable infusion pump for selectively dispensing a drug.

19. The system of claim 18 wherein the drug comprises insulin.

20. The system of claim 1 wherein the medical device comprises an implantable sensor for sensing a selected state of the body.

21. The system of claim 20 wherein the sensor comprises a glucose sensor.

22. The system of claim 1 wherein the medical device comprises an implantable electrode for selectively stimulating a portion of the body of the patient.

23. The system of claim 1,
wherein a message is sent using one of a predefined plurality of preambles.

24. The system of claim 23 wherein a first portion of the MD telemetry system is incorporated into the MD processor and a second portion of the MD telemetry system is external to the MD processor, or wherein a first portion of the CD telemetry system is incorporated into the CD processor and a second portion of the CD telemetry system is external to the CD processor.

25. The system of claim 24 wherein (1) the MD electronic control circuitry comprises at least one external MD functional module, other than the second portion of the MD telemetry system, that is external to the MD processor, (2) the CD electronic control circuitry comprises at least one external CD functional module, other than the second portion of the CD telemetry system, that is external to the CD processor, (3) the MD processor comprises an internal MD CPU and at least one other internal MD functional module, or (4) the CD processor comprises an internal CD CPU and at least one other internal CD functional module.

26. The system of claim 23 wherein the medical device comprises an implantable infusion pump for selectively dispensing a drug.

27. The system of claim 26 wherein the drug comprises insulin.

28. The system of claim 23 wherein the medical device comprises an implantable sensor for sensing a selected state of the body.

29. The system of claim 28 wherein the sensor comprises a glucose sensor.

30. The system of claim 23 wherein the medical device comprises an implantable electrode for selectively stimulating a portion of the body of the patient.

31. The system of claim 23 wherein at least a portion of the plurality of preambles comprise different bit patterns.

32. The system of claim 31 wherein at least one bit pattern comprises a sequence that includes repeated use of a pattern of 10 or 01 and at least one other bit pattern comprises a sequence that includes repeat use of a pattern of 110, 011, 001, or 100.

33. The system of claim 23 wherein at least a portion of the plurality of preambles comprise bit patterns of different lengths.

34. The system of claim 23 wherein a message is sent from the communication device to the medical device using a first preamble and wherein a message is sent form the medical device to the communication device using a second preamble wherein the first and second preambles are different.

35. The system of claim 34 wherein the first preamble comprises a sequence that includes repeated use of a pattern of 110 and wherein the second preamble comprises a sequence that includes repeated use of a pattern of 10.

36. The system of claim 34 wherein at least a portion of the preambles of messages sent to the medical device from the communication device have preambles of varying length.

37. The system of claim 34 wherein the preambles of messages sent to the communication device by the medical device have fixed lengths.

38. The system of claim 37 wherein at least some of the plurality of preambles comprise both different bit patterns and different lengths.

39. The system of claim 23 wherein a first preamble is used to send at least some messages from the communication device to the medical device and a second preamble, which is different from the first preamble, is used to send at least some messages from the medical device to the communication device.

40. The system of claim 23 wherein messages are sent from the communication device to the medical device using at least two different preamble lengths.

41. The system of claim 40 wherein a first preamble captures holds the attention of the MD telemetry system and as long as it continues to be received.

42. The system of claim 40 wherein a second preamble is of a different pattern than the first preamble and does not hold the attention of the MD telemetry system beyond a prescribed inbound listening period.

* * * * *